United States Patent [19]
Wehner et al.

[11] Patent Number: 6,002,004
[45] Date of Patent: Dec. 14, 1999

[54] PYRROLODIAZINE DERIVATIVES AS STABILIZERS FOR CHLORINE-CONTAINING POLYMERS

[75] Inventors: Wolfgang Wehner, Ober-Ramstadt; Hans-Helmut Friedrich, Lautertal; Rolf Drewes, Lindenfels, all of Germany

[73] Assignee: Witco Vinyl Additives GmbH, Lampertheim, Germany

[21] Appl. No.: 09/007,196

[22] Filed: Jan. 14, 1998

Related U.S. Application Data

[62] Division of application No. 08/618,591, Mar. 20, 1996.

[30] Foreign Application Priority Data

Mar. 28, 1995 [EP] European Pat. Off. ............ 958102048

[51] Int. Cl.$^6$ .................................................. C07D 487/04
[52] U.S. Cl. .............................................. 544/280
[58] Field of Search ............................................. 544/280

[56] References Cited

U.S. PATENT DOCUMENTS

| | | | |
|---|---|---|---|
| 3,398,114 | 8/1968 | Pollack | 524/91 |
| 3,897,433 | 7/1975 | Dupont et al. | 260/256.4 F |
| 4,369,276 | 1/1983 | Wirth et al. | 524/104 |
| 4,859,724 | 8/1989 | Cantatore et al. | 524/91 |
| 5,084,499 | 1/1992 | Todd et al. | 524/414 |
| 5,155,152 | 10/1992 | Wehner et al. | 524/100 |
| 5,235,053 | 8/1993 | Barnett et al. | 544/280 |
| 5,288,776 | 2/1994 | Drewes et al. | 524/94 |

OTHER PUBLICATIONS

Quijano et al., J. Heterocycl. Chem. (1990), 27(4), 1079–83, 1990.
Chem. Abstract 123:170044t[I. Votruba, et al., Collect. Czech. Chem. Commun. 1994, 59(10), 2303–2330].
Chem. Abstract 123:285616y [J. Heterocycl. Chem. 1995, 32 (3), 1043–1049].
N. M. Smimova et al., Chemistry of Heterocyclic Compounds, p. 443–446, (1978).
H. Ogura et al., Chem. Pharm. Bull., vol. 20 (2), p. 404–408, (1972).
S. Senda et al., Chem. Pharm. Bull., vol. 22 (12), p. 2921–2928, (1974).
Chem. Pharm. Bull., vol. 20, No. 2, pp. 404–408, (1972).
Chem. Pharm. Bull., vol. 22, No. 12, pp. 2921–2928, (1974).
S. Senda et al., Chem. Pharm. Bull., vol. 22(7), p. 1459–1467, (1974).
F. Yoneda et al., Chem. Pharm. Bull., vol. 21(3), p. 473–477, (1973).
K. Hirota et al., Synthesis, p.1097–1099, (1982).

*Primary Examiner*—Mukund J. Shah
*Assistant Examiner*—Bruck Kifle
*Attorney, Agent, or Firm*—Scully, Scott, Murphy & Presser

[57] ABSTRACT

The invention relates to compositions comprising
  a) a chlorine-containing polymer and
  b) at least one compound containing at least one radical of the formula I

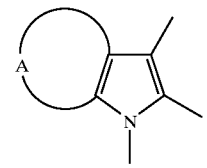

(I)

in which A is the additional groups or atoms necessary to form an unsubstituted or substituted six-membered heterocyclic ring containing two nitrogen ring atoms.

4 Claims, No Drawings

PYRROLODIAZINE DERIVATIVES AS STABILIZERS FOR CHLORINE-CONTAINING POLYMERS

This application is a divisional of prior application Ser. No. 08/618,591 filed Mar. 20, 1996.

The present invention relates to compositions comprising a chlorine-containing polymer, preferably PVC, and a pyrrolodiazine derivative as stabilizer, to the use thereof for stabilizing chlorine-containing polymers against oxidative, thermal or photoinduced degradation, to a process for stabilizing PVC moulding compositions, to a process for the preparation of the stabilizers, and to novel pyrrolodiazine derivatives.

It is known that chlorine-containing polymers must be protected against the harmful effect of light and heat, in particular during conversion into mouldings. Some pyrrole derivatives and their use as costabilizers have been described, for example in U.S. Pat. No. 4,369,276, U.S. Pat. No. 5,155,152 or U.S. Pat. No. 5,288,776.

These known stabilizers and stabilizer mixtures are not satisfactory in all respects in chlorine-containing polymers.

Some pyrrolodiazine derivatives are known and are described, for example, in the following publications: N. M. Smirnova, L. F. Linberg, V. M. Nesterov und T. S. Safanova, Chemistry of Heterocyclic Compounds 1978, 443–446; H. Ogura, M. Sakaguchi and K. Takeda, Chem. Pharm. Bull. 20 (2), 404–408 (1972); S. Senda and K. Hirota, Chem. Pharm. Bull. 22 (12), 2921–28 (1974); S. Senda and K. Hirota, Chem. Pharm. Bull. 22 (7), 1459–1467 (1974); or F. Yoneda, M. Higuchi, K. Senga, M. Kanohori and S. Nishigaki, Chem. Pharm. Bull. 21 (3), 473–477 (1973).

It has now been found that pyrrolodiazine derivatives are particularly suitable as stabilizers for chlorine-containing polymers, in particular for PVC.

The invention therefore relates to compositions comprising a) a chlorine-containing polymer and b) at least one compound containing at least one radical of the formula I

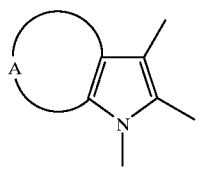

(I)

in which A is the additional groups or atoms necessary to form an unsubstituted or substituted six-membered heterocyclic ring containing two nitrogen ring atoms.

A as the additional groups or atoms necessary to make up an unsubstituted or substituted six-membered heterocyclic ring containing two nitrogen ring atoms in the formula I is, for example, a group of the formula a, b, c, d, e, f or g

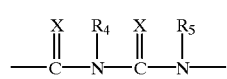

(a)

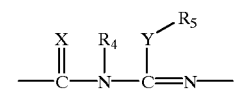

(b)

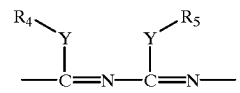

(c)

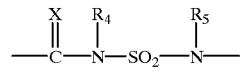

(d)

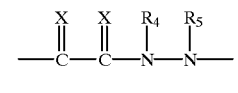

(e)

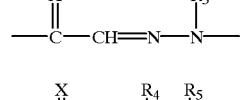

(f)

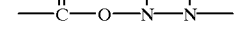

(g)

in which

X is oxygen or sulfur,

Y is oxygen, sulfur or

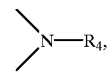

$R_4$ and $R_5$, independently of one another, are hydrogen, $C_1$–$C_{12}$alkyl, $C_2$–$C_{12}$alkyl which is interrupted by oxygen, sulfur or carboxyl; hydroxyl-substituted $C_1$–$C_{12}$alkyl; $C_3$–$C_6$alkenyl, $C_5$–$C_8$cycloalkyl which is unsubstituted or substituted by one to three $R_6$ radicals; phenyl which is unsubstituted or substituted by one to three $R_6$ radicals; or $C_7$–$C_9$phenyl-alkyl which is unsubstituted or substituted on the phenyl ring by one to three $R_6$ radicals, and $R_6$ is $C_1$–$C_4$alkyl, $C_1$–$C_4$alkoxy, $C_5$–$C_8$cycloalkyl, hydroxyl or chlorine.

The compounds containing at least one of the radicals of the formula I are distinguished by a very good stabilizing action to oxidative, thermal and photoinduced degradation in chlorine-containing polymers. The colour-stabilizing action on heating is particularly noteworthy.

Of interest are compositions in which component b) is at least one compound of the formula II

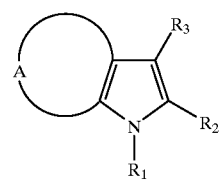

(II)

in which

A is a group of the formula III or IV

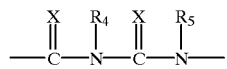  (III)

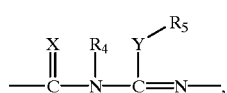  (IV)

X is oxygen or sulfur,

Y is oxygen, sulfur or

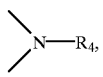

$R_1$ is hydrogen, $C_1$–$C_{12}$alkyl, $C_2$–$C_{12}$alkyl which is interrupted by oxygen, sulfur or carboxyl; hydroxyl-substituted $C_1$–$C_{12}$alkyl; $C_3$–$C_6$alkenyl, $C_5$–$C_8$cycloalkyl which is unsubstituted or substituted by one to three $R_6$ radicals; phenyl which is unsubstituted or substituted by one to three $R_6$ radicals; $C_7$–$C_9$phenylalkyl which is unsubstituted or substituted on the phenyl ring by one to three $R_6$ radicals;

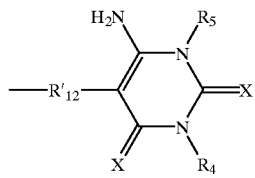

or a radical of the formula V or VI

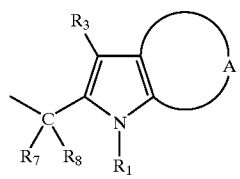  (V)

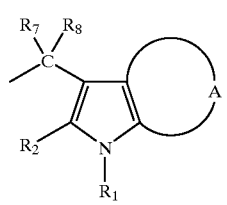  (VI)

in which A and $R_1$ are as defined above, or furthermore one of the radicals $R_2$ and $R_3$ is hydroxyl, formyl, $C_1$–$C_{12}$alkoxy, phenoxy which is unsubstituted or substituted by one to three $R_6$ radicals; $C_1$–$C_{12}$alkanoyloxy, benzoyloxy which is unsubstituted or substituted by one to three $R_6$ radicals;

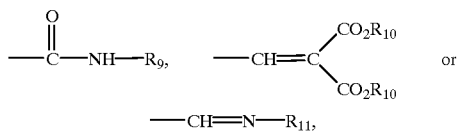

$R_4$ and $R_5$, independently of one another, are hydrogen, $C_1$–$C_{12}$alkyl, $C_2$–$C_{12}$alkyl which is interrupted by oxygen, sulfur or carboxyl; hydroxyl-substituted $C_1$–$C_{12}$alkyl; $C_3$–$C_6$alkenyl, $C_5$–$C_8$cycloalkyl which is unsubstituted or substituted by one to three $R_6$ radicals; phenyl which is unsubstituted or substituted by one to three $R_6$ radicals; or $C_7$–$C_9$phenyl-alkyl which is unsubstituted or substituted on the phenyl ring by one to three $R_6$ radicals, $R_6$ is $C_1$–$C_4$alkyl, $C_1$–$C_4$alkoxy, $C_5$–$C_8$cycloalkyl, hydroxyl or chlorine, $R_7$ and $R_8$, independently of one another, are hydrogen, $CF_3$, $C_1$–$C_{12}$alkyl, phenyl or $C_7$–$C_9$phenylalkyl, or $R_7$ and $R_8$, together with the carbon atom to which they are bonded, form an unsubstituted or $C_1$–$C_4$alkyl-substituted $C_5$–$C_{12}$cycloalkylidene ring, $R_9$ is phenyl which is unsubstituted or substituted by one to three $R_6$ radicals; $R_{10}$ is hydrogen, $C_1$–$C_{12}$alkyl, $C_2$–$C_{12}$alkyl which is interrupted by oxygen or sulfur, hydroxyl-substituted $C_1$–$C_{12}$alkyl; $C_3$–$C_6$alkenyl, $C_5$–$C_9$cycloalkyl which is unsubstituted or substituted by one to three $R_6$ radicals; phenyl which is unsubstituted or substituted by one to three $R_6$ radicals; or $C_7$–$C_9$phenylalkyl which is unsubstituted or substituted on the phenyl ring by one to three $R_6$ radicals, $R_{11}$ is $C_1$–$C_{12}$alkyl, $C_2$–$C_{12}$alkyl which is interrupted by oxygen or sulfur, hydroxyl-substituted $C_1$–$C_2$alkyl; $C_3$–$C_6$alkenyl, $C_5$–$C_8$cycloalkyl which is unsubstituted or substituted by one to three $R_6$ radicals; phenyl which is unsubstituted or substituted by one to three $R_6$ radicals; or $C_7$–$C_9$phenylalkyl which is unsubstituted or substituted on the phenyl ring by one to three $R_6$ radicals, $R'_{12}$ is a direct bond or

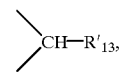

and $R'_{13}$ is hydrogen or $C_1$–$C_8$alkyl.

The compounds of the formula II in which A is a radical of the formula III or IV have the formulae VII, VIIa, VIII or VIIIa.

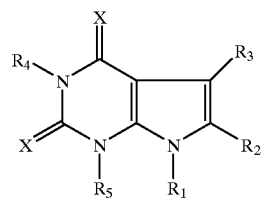  (VII)

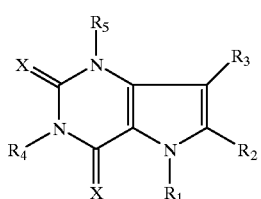

(VIIa)

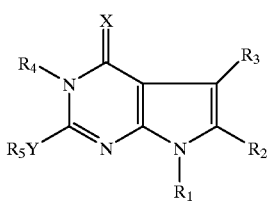

(VIII)

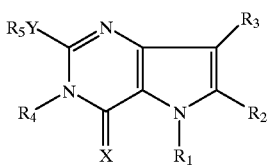

(VIIIa)

Alkyl having up to 12 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl or 1,1,3,3,5,5-hexamethylhexyl. One of the preferred meanings of $R_1$, $R_2$, $R_3$, $R_4$, $R_5$, $R_7$, $R_8$, $R_{10}$ and $R_{11}$ is, for example, $C_1$–$C_{10}$alkyl, in particular $C_1$–$C_8$alkyl, for example $C_1$–$C_6$alkyl. A particularly preferred meaning of $R_1$, $R_2$, $R_3$, $R_4$ and $R_5$ is $C_1$–$C_4$alkyl.

Alkyl having 2 to 12 carbon atoms which is interrupted by oxygen, sulfur or carboxyl can be mono- or polyinterrupted and is, for example, $CH_3$—O—$CH_2$—, $CH_3$—S—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$—, $CH_3$—(O—$CH_2CH_2$—)$_4$O—$CH_2$—, $CH_3CO_2CH_2CH_2$— or $CH_3CH_2CO_2CH_2CH_2$—. A particularly preferred meaning of $R_1$, $R_2$, $R_3$, $R_4$, $R_5$, $R_{10}$ and $R_{11}$ is, for example, $C_2$–$C_{12}$alkyl which is interrupted by oxygen, in particular $C_4$–$C_{12}$alkyl which is interrupted by oxygen, for example $C_4$–$C_{10}$alkyl which is interrupted by oxygen.

Hydroxyl-substituted alkyl having up to 12 carbon atoms which preferably contains 1 to 3, in particular 1 or 2, hydroxyl groups, is a branched or unbranched radical, for example 2-hydroxyethyl, 2-hydroxypropyl, 3-hydroxypropyl, 2,3-dihydroxypropyl, 2-hydroxybutyl, 2-hydroxypentyl, 2-hydroxyhexyl, 2-hydroxyheptyl, 2-hydroxyoctyl or 2,5,6-trihydroxyhexyl. A particularly preferred meaning of $R_1$, $R_2$, $R_3$, $R_4$, $R_5$, $R_{10}$ and $R_{11}$ is, for example, hydroxyl-substituted $C_1$–$C_{10}$alkyl, in particular $C_2$–$C_8$alkyl. Particular preference is given to 2-hydroxyethyl.

Alkenyl having 3 to 6 carbon atoms is a branched or unbranched radical, for example propenyl, 2-butenyl, 3-butenyl, isobutenyl, n-2,4-pentadienyl, 3-methyl-2-butenyl, 2-pentenyl or 2-hexenyl. A particularly preferred meaning of $R_1$, $R_2$, $R_3$, $R_4$, $R_5$, $R_{10}$ and $R_{11}$ is propenyl.

$C_5$–$C_8$Cycloalkyl which is unsubstituted or substituted by one to three $R_6$ radicals and contains, in particular, 1 or 2 branched or unbranched $C_1$–$C_4$alkyl radicals is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Preference is given to cyclohexyl.

Phenyl which is substituted by 1 to 3 $R_6$ radicals and preferably contains 1 or 2 $C_1$–$C_4$alkyl groups is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$–$C_9$Phenylalkyl which is unsubstituted or substituted on the phenyl ring by 1 to 3 $R_6$ radicals and contains, in particular, 1 or 2 branched or unbranched $C_1$–$C_4$alkyl groups is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

Alkoxy having up to 12 carbon atoms is a branched or unbranched radical, for example methoxy, ethoxy, propoxy, isopropoxy, n-butoxy, isobutoxy, pentoxy, isopentoxy, hexyloxy, heptyloxy, octyloxy, decyloxy, tetradecyloxy, hexadecyloxy or octadecyloxy. A preferred meaning of $R_2$ and $R_3$ is alkoxy having 1 to 10, in particular 1 to 8, carbon atoms. A preferred meaning of $R_6$ is methoxy.

Phenoxy which is substituted by one to three $R_6$ radicals and preferably contains 1 or 2 $C_1$–$C_4$alkyl groups is, for example, o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

Alkanoyloxy having up to 12 carbon atoms is a branched or unbranched radical, for example formyloxy, acetoxy, propionyloxy, butanoyloxy, pentanoyloxy, hexanoyloxy, heptanoyloxy, octanoyloxy, nonanoyloxy, decanoyloxy, undecanoyloxy or dodecanoyloxy. Preference is given to alkanoyloxy having 1 to 10, in particular 1 to 8, for example 2 to 6, carbon atoms. Particular preference is given to acetoxy.

Benzoyloxy which is substituted by one to three $R_6$ radicals and carries, in particular, 1 or 2 $C_1$–$C_4$alkyl groups is, for example, o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy.

An alkali metal is, for example, lithium, sodium, potassium, rubidium or caesium. Preference is given to sodium and potassium.

An alkaline earth metal is, for example, magnesium, calcium, strontium or barium. Preference is given to magnesium and calcium.

A $C_1$–$C_4$alkyl-substituted $C_5$–$C_{12}$cycloalkylidene ring which preferably contains 1 to 3, in particular 1 or 2 branched or unbranched alkyl groups is, for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene and tert-butylcyclohexylidene.

Preference is given to compositions in which component b) is at least one compound of the formula II, in which the compound of the formula II is a compound of the formula VII, VIIa or VIII (VII)

(VIIa)

(VIII)

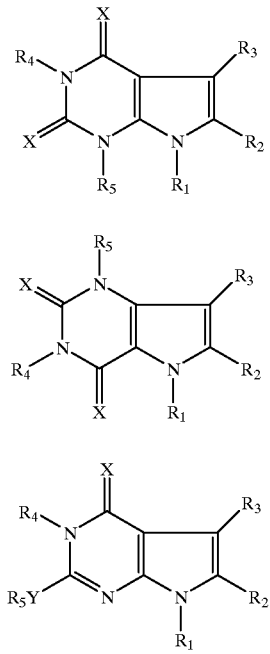

in which

X is oxygen or sulfur,

Y is oxygen, sulfur or

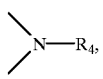

$R_1$ is hydrogen, $C_1$–$C_{10}$alkyl, $C_2$–$C_{12}$alkyl which is interrupted by oxygen; hydroxyl-substituted $C_1$–$C_{10}$alkyl; $C_3$–$C_6$alkenyl, $C_5$–$C_8$cycloalkyl, phenyl, $C_7$–$C_9$phenylalkyl, an alkali metal or an alkaline earth metal, $R_2$ and $R_3$, independently of one another, are hydrogen, $C_1$–$C_{10}$alkyl, $C_2$–$C_{12}$alkyl which is interrupted by oxygen; hydroxyl-substituted $C_1$–$C_{10}$alkyl; $C_3$–$C_6$alkenyl, $C_5$–$C_8$cycloalkyl, phenyl, $C_7$–$C_9$phenylalkyl which is unsubstituted or substituted on the phenyl ring by one to three $R_6$ radicals;

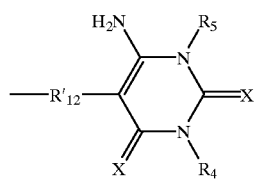

or a radical of the formula IX, X, XI or XII (IX)

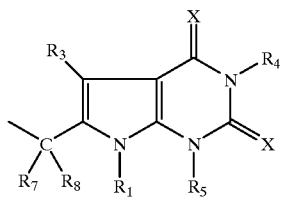

(X)

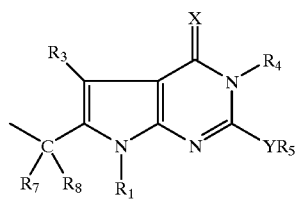

(XI)

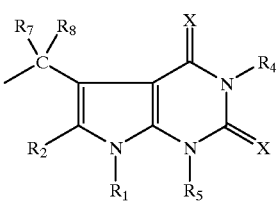

(XII)

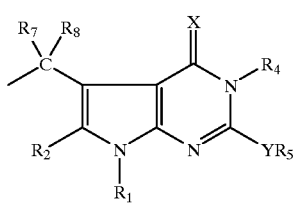

in which X, Y, $R_1$, $R_2$ and $R_3$ are as defined above, or furthermore one of the radicals $R_2$ and $R_3$ is hydroxyl, formyl, $C_1$–$C_{10}$alkoxy, phenoxy, $C_1$–$C_{10}$alkanoyloxy, benzoyloxy,

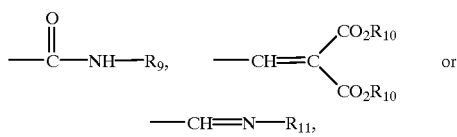

$R_4$ and $R_5$, independently of one another, are hydrogen, $C_1$–$C_{10}$alkyl, $C_2$–$C_{12}$alkyl which is interrupted by oxygen; hydroxyl-substituted $C_1$–$C_{10}$alkyl; $C_3$–$C_6$alkenyl, $C_5$–$C_8$cycloalkyl, phenyl, or $C_7$–$C_9$phenylalkyl, $R_6$ is $C_1$–$C_4$alkyl, $C_1$–$C_4$alkoxy, cyclohexyl, hydroxyl or chlorine, $R_7$ and $R_8$, independently of one another, are hydrogen, $C_1$–$C_{10}$alkyl, phenyl or $C_7$–$C_9$phenylalkyl, $R_9$ is phenyl, $R_{10}$ is $C_1$–$C_{10}$alkyl, $C_2$–$C_{12}$alkyl which is interrupted by oxygen; $C_3$–$C_6$alkenyl, $C_5$–$C_8$cycloalkyl, phenyl or $C_7$–$C_9$phenylalkyl, $R_{11}$ is $C_1$–$C_{10}$alkyl, $C_5$–$C_8$cycloalkyl, phenyl or $C_7$–$C_9$phenylalkyl, $R'_{12}$ is a direct bond or

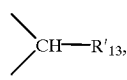

and $R'_{13}$ is hydrogen or $C_1$–$C_4$alkyl.

Preference is also given to compositions in which, in the formula II, X and Y are oxygen.

Preference is likewise given to compositions in which, in the formula II, $R_1$ is hydrogen, $C_1$–$C_4$alkyl, benzyl, 2-hydroxyethyl, sodium, magnesium or calcium.

Likewise of interest are compositions in which, in the formula II, $R_2$ is hydrogen, $C_1$–$C_4$alkyl, phenyl, 2,6-di-tert-butyl-4-hydroxybenzyl, hydroxyl,

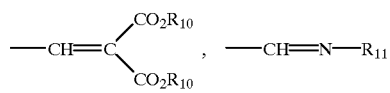

or a radical of the formula IX

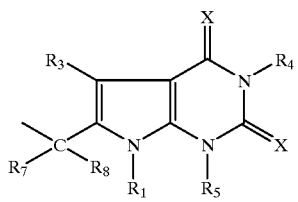

(IX)

in which X, $R_1$, $R_4$, $R_5$, $R_7$, $R_8$, $R_{10}$ and $R_{11}$ are as defined in claim 2, and $R_3$ is hydrogen, hydroxyl, $C_1$–$C_4$alkyl, phenyl,

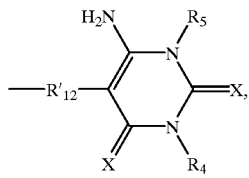

in which X, $R_4$, $R_5$ and $R'_{12}$ are as defined in claim 2, or 2,6-di-tert-butyl-4-hydroxybenzyl.

Of particular interest are compositions in which, in the formula II, $R_4$ and $R_5$, independently of one another, are hydrogen or $C_1$–$C_4$alkyl.

Of especial interest are compositions in which component b) is at least one compound of the formula VII, VIIa or VIII in which X and Y are oxygen, $R_1$ is hydrogen, $C_1$–$C_4$alkyl, hydroxyl-substituted $C_2$–$C_6$alkyl, an alkali metal or an alkaline earth metal, $R_2$ is hydrogen, $C_1$–$C_8$alkyl, phenyl which is unsubstituted or substituted by $C_1$–$C_4$alkyl; 2,6-di-tert-butyl-4-hydroxybenzyl, hydroxyl,

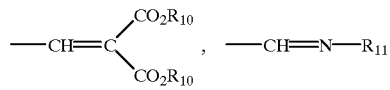

or a radical of the formula IX

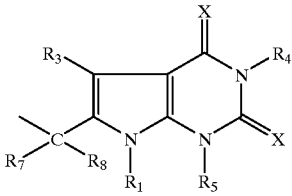

(IX)

in which X and $R_1$ are as defined above, $R_3$ is hydrogen, hydroxyl, $C_1$–$C_8$alkyl, phenyl which is unsubstituted or substituted by $C_1$–$C_4$alkyl;

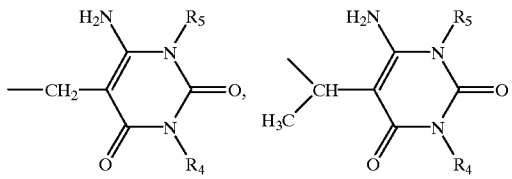

or 2,6-di-tert-butyl-4-hydroxybenzyl, $R_4$ and $R_5$, independently of one another, are hydrogen, $C_1$–$C_4$alkyl, $C_3$–$C_6$alkenyl or benzyl, $R_7$ and $R_8$, independently of one another, are hydrogen, $C_1$–$C_9$alkyl or phenyl, or $R_7$ and $R_8$, together with the carbon atom to which they are bonded, form a $C_5$–$C_8$cycloalkylidene ring, $R_{10}$ is $C_1$–$C_8$alkyl, and $R_{11}$ is $C_7$–$C_9$phenylalkyl.

Of very especial interest are compositions in which component b) is at least one compound of the formula VII, VIIa or VIII in which X and Y are oxygen, $R_1$ is hydrogen, 2-hydroxyethyl, sodium, magnesium or calcium, $R_2$ is hydrogen, $C_1$–$C_4$alkyl, phenyl, 2,6-di-tert-butyl-4-hydroxybenyl, hydroxyl,

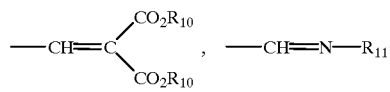

or a radical of the formula IX

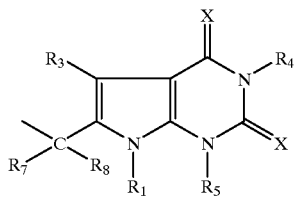
(IX)

in which X and $R_1$ are as defined above, $R_3$ is hydrogen, hydroxyl, $C_1$–$C_4$alkyl, phenyl,

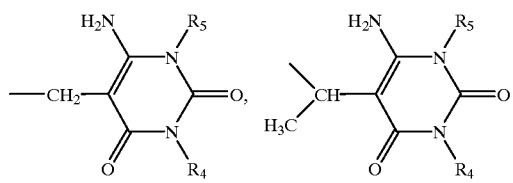

or 2,6-di-tert-butyl-4-hydroxybenzyl, $R_4$ and $R_5$, independently of one another, are hydrogen or $C_1$–$C_4$alkyl, $R_7$ and $R_8$, independently of one another, are hydrogen, $C_1$–$C_9$alkyl or phenyl, $R_{10}$ is $C_1$–$C_4$alkyl, and $R_{11}$ is benzyl.

Especial preference is given to compositions in which component b) is at least one compound of the formula VII in which the compound of the formula VII is

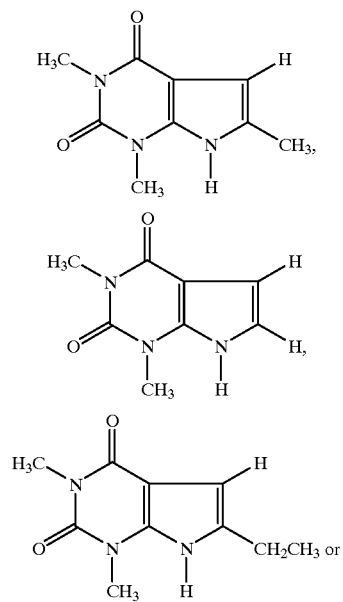

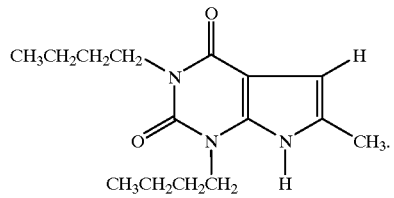

The chlorine-containing polymers can be the following list of examples: polymers of vinyl chloride, vinyl resins containing vinyl chloride units in their structure, such as copolymers of vinyl chloride and vinyl esters of aliphatic acids, in particular vinyl acetate, copolymers of vinyl chloride with esters of acrylic and methacrylic acid and with acrylonitrile, copolymers of vinyl chloride with diene compounds and unsaturated dicarboxylic acids or anhydrides thereof, such as copolymers of vinyl chloride with diethyl maleate, diethyl fumarate or maleic anhydride, post-chlorinated polymers and copolymers of vinyl chloride, copolymers of vinyl chloride and vinylidene chloride with unsaturated aldehydes, ketones and others, such as acrolein, crotonaldehyde, vinyl methyl ketone, vinyl methyl ether, vinyl isobutyl ether and similar; polymers of vinylidene chloride and copolymers thereof with vinyl chloride and other polymerizable compounds; polymers of vinyl chloroacetate and dichlorodivinyl ether; chlorinated polymers of vinyl acetate, chlorinated polymeric esters of acrylic acid and alpha-substituted acrylic acid; polymers of chlorinated styrenes, for example dichlorostyrene; chlorinated rubbers; chlorinated polymers of ethylene; polymers and post-chlorinated polymers of chlorobutadiene and copolymers thereof with vinyl chloride, rubber hydrochloride and chlorinated rubber hydrochloride; and mixtures of said polymers with one another or with other polymerizable compounds.

Also included are graft polymers of PVC with EVA, ABS and MBS. Preferred substrates are also mixtures of the abovementioned homopolymers and copolymers, in particular vinyl chloride homopolymers, with other thermoplastic and/or elastomeric polymers, in particular blends with ABS, MBS, NBR, SAN, EVA, CPE, MBAS, PMA, PMMA, EPDM and polylactones.

The chlorine-containing polymer is particularly preferably polyvinyl chloride, in particular a suspension polymer and bulk polymer.

For the purposes of this invention, component a) is also taken to mean, in particular, recycled chlorine-containing polymers, these being the polymers described in greater detail above which have experienced damage due to processing, use or storage. Particular preference is given to recycled PVC. Recycled materials can also contain small amounts of foreign substances, for example paper, pigments or adhesives, which are frequently difficult to remove. These foreign substances can also originate from contact with diverse substances during use or processing, for example fuel residues, paint components, metal traces, initiator residues or water traces.

It is possible to employ the compounds containing at least one radical of the formula I alone or preferably together with known heat stabilizers, for example organotin compounds, organoantimony compounds, Me(II) phenoxides, in particular $C_7$–$C_{20}$alkylphenoxides, for example nonylphenoxide, or Me(II) carboxylates. Me(II) is, for example, Ba, Ca, Mg or Zn. The carboxylates are preferably salts of carboxylic acids having 7 to 20 carbon atoms, for example benzoates, alkenoates or alkanoates, preferably stearates, oleates, laurates, palmitates, hydroxystearates, dihydroxystearates or 2-ethylhexanoates. Particular preference is given to stearates, oleates and p-tert-butylbenzoates. Examples of organotin compounds and organoantimony compounds are the compounds mentioned in U.S. Pat. No. 4,743,640, column 3, line 48, to column 5, line 38.

In addition, the chlorine-containing polymers stabilized by the compounds containing at least one radical of the formula I can also contain further conventional PVC stabilizers or PVC costabilizers in conventional amounts, for example phosphites or phosphonites, epoxide compounds, such as glycidyl compounds, perchlorate salts, hydrotalcites and/or zeolites.

The phosphites are preferably those of the formulae

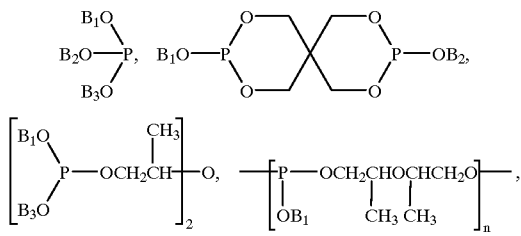

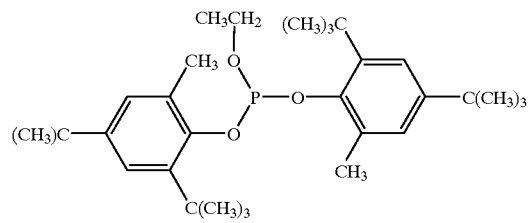

in which $B_1$, $B_2$ and $B_3$, independently of one another, are $C_4$–$C_{18}$alkyl, $C_6$–$C_{18}$alkenyl, $C_5$–$C_7$cycloalkyl, phenyl or phenyl which is substituted by one to three $C_1$–$C_{12}$alkyl groups.

Examples are trioctyl, tridecyl, tridodecyl, tritetradecyl, tristearyl, trioleyl, triphenyl, tricresyl, tris-p-nonylphenyl and tricyclohexyl phosphite. Preference is given to aryl dialkyl and alkyl diaryl phosphites, for example phenyl didecyl, (2,4di-tert-butylphenyl) didodecyl, (2,6-di-tert-butylphenyl) didodecyl phosphite, and dialkyl and diaryl pentaerythrityl diphosphites, for example distearyl pentaerythrityl diphosphite. Also preferred are tetraphenyl and tetraalkyl dipropylene 1,2-glycol diphosphites and poly[dipropylene 1,2-glycol phenyl phosphites] and poly[dipropylene 1,2-glycol alkyl phosphites].

Particularly preferred organic phosphites are distearyl pentaerythrityl diphosphite, tris(nonylphenyl) phosphite, phenyl didecyl phosphite, tetraphenyl dipropylene 1,2-glycol diphosphite and poly[dipropylene 1,2-glycol phenyl phosphite].

Especial preference is also given to phosphates or phosphonites of the following formulae:

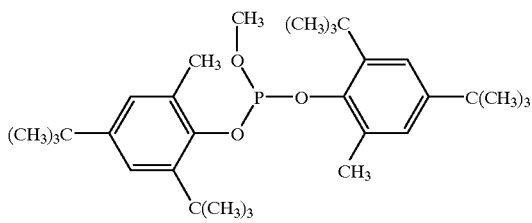

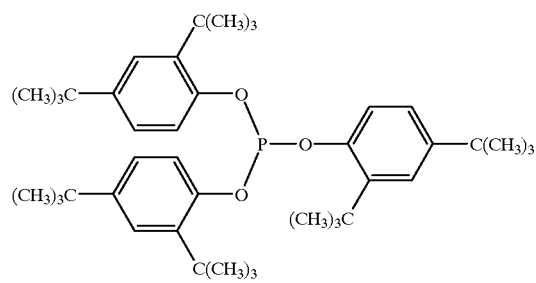

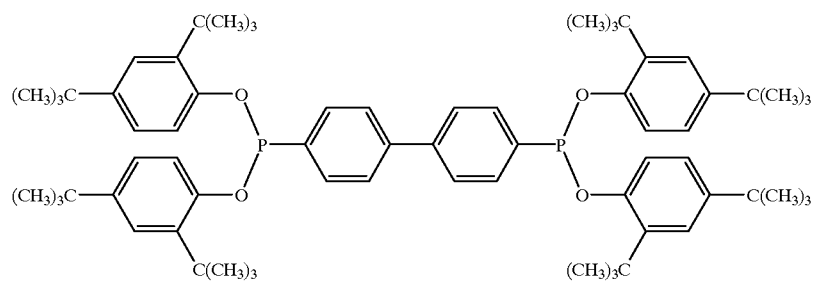

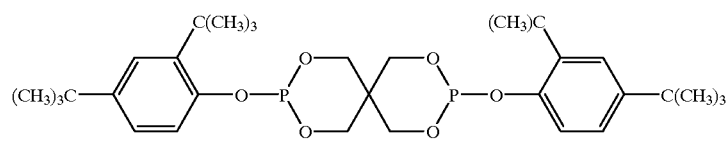

-continued

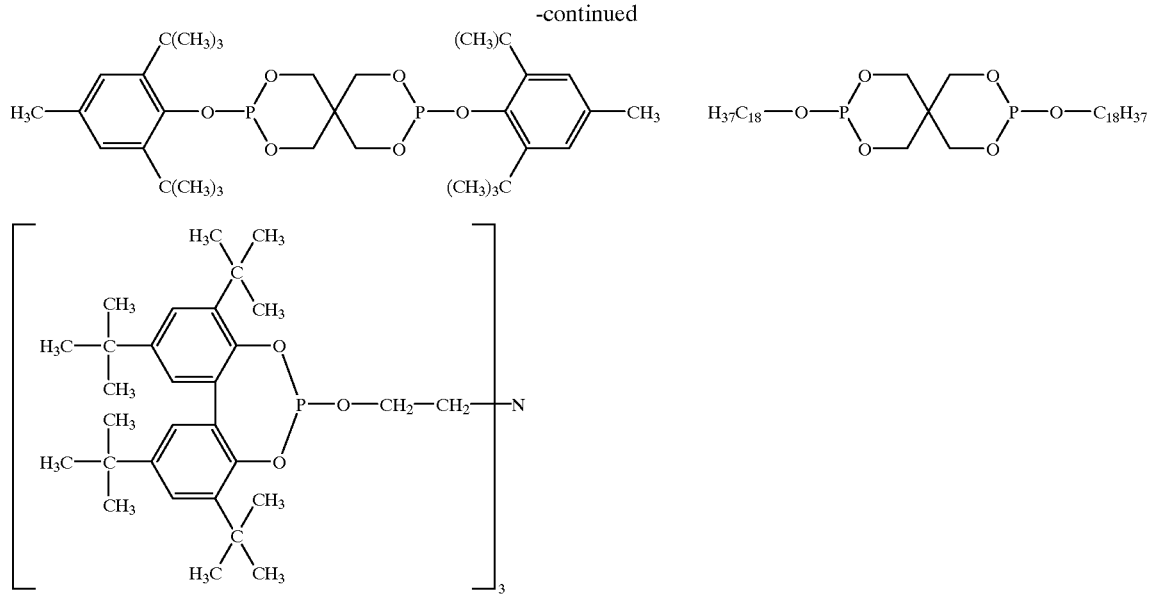

The phosphites or phosphonites are employed in an amount of, for example, from 0.3 to 5 parts by weight, preferably from 0.5 to 1 part by weight, based on 100 parts by weight of PVC.

The epoxide compounds are preferably epoxidized oils and epoxidized fatty acid esters, for example epoxidized polybutadiene, epoxidized soya oil, epoxidized linseed oil, epoxidized rapeseed oil, epoxidized tallow, methylbutyl or 2-ethylhexyl epoxystearate, tris(epoxypropyl)isocyanurate, epoxidized castor oil, epoxidized sunflower oil, 3-(2-xenoxy)-1,2-epoxypropane, bisphenol A polyglycidyl ether, vinylcyclohexene diepoxide, dicyclopentadiene diepoxide and 3,4-epoxycyclohexylmethyl 3,4-epoxycyclohexanecarboxylate.

The glycidyl compounds which can be used for the purposes of the invention can have an aliphatic, aromatic, cycloaliphatic, araliphatic or heterocyclic structure; they contain epoxide groups as side groups. The epoxide groups are preferably bonded to the remainder of the molecule as glycidyl groups via ether or ester bonds, or they are N-glycidyl derivatives of heterocyclic amines, amides or imides. Epoxide compounds of these types are known in general terms and are commercially available.

The terminal epoxide compounds contain at least one epoxy radical, in particular of the formula I'

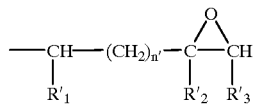

(I')

which is bonded directly to carbon, oxygen, nitrogen or sulfur atoms, where $R'_1$ and $R'_3$ are both hydrogen, $R'_2$ is hydrogen or methyl, and n' is 0, or in which $R'_1$ and $R'_3$ together are —CH$_2$—CH$_2$— or —CH$_2$—CH$_2$—CH$_2$—, $R'_2$ is then hydrogen, and n' is 0 or 1.

Examples of terminal epoxide compounds which may be mentioned are:

I) Glycidyl and β-methylglycidyl esters obtainable by reacting a compound containing at least one carboxyl group in the molecule and epichlorohydrin or glycerol dichlorohydrin or β-methylepichlorohydrin. The reaction is preferably carried out in the presence of bases.

The compounds which are containing at least one carboxyl group in the molecule used can be aliphatic carboxylic acids. Examples of these carboxylic acids are glutaric acid, adipic acid, pimelic acid, suberic acid, azelaic acid, sebacic acid or dimerized or trimerized linoleic acid, acrylic acid, methacrylic acid, caproic acid, caprylic acid, lauric acid, myristic acid, palmitic acid, stearic acid and pelargonic acid, and the acids mentioned in the case of the organozinc compounds.

However, it is also possible to employ cycloaliphatic carboxylic acids, for example cyclohexanecarboxylic acid, tetrahydrophthalic acid, 4-methyltetrahydrophthalic acid, hexahydrophthalic acid or 4-methylhexahydrophthalic acid.

It is also possible to use aromatic carboxylic acids, for example benzoic acid, phthalic acid, isophthalic acid, trimellitic acid or pyromellitic acid.

It is likewise possible to use carboxyl-terminated adducts, for example of trimellitic acid and polyols, for example glycerol or 2,2-bis(4-hydroxycyclohexyl)propane.

Other epoxide compounds which can be used for the purposes of the present invention are given in EP 0 506 617.

II) Glycidyl or β-methylglycidyl ethers obtainable by reacting a compound containing at least one free alcoholic hydroxyl group and/or phenolic hydroxyl group and a suitably substituted epichlorohydrin under alkaline conditions, or in the presence of an acid catalyst followed by alkali treatment.

Ethers of this type are derived, for example, from acyclic alcohols, such as ethylene glycol, diethylene glycol and higher poly(oxyethylene) glycols, propane-1,2-diol or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, bistrimethylolpropane, pentaerythritol, sorbitol, and from polyepichlorohydrins, butanol, amyl alcohol, pentanol and from monofunctional alcohols such as isooctanol, 2-ethylhexanol, isodecanol and $C_7$–$C_9$alkanol and $C_9$–$C_{11}$alkanol mixtures.

However, they are also derived, for example, from cycloaliphatic alcohols, such as 1,3- or 1,4- dihydroxycyclohexane, bis(4-hydroxycyclohexyl)methane, 2,2-bis(4-hydroxycyclohexyl)propane or 1,1-bis(hydroxymethyl)cyclohex-3-ene, or they contain aromatic rings, such as N,N-bis(2-hydroxyethyl)aniline or p,p'-bis(2-hydroxyethylamino)diphenylmethane.

The terminal epoxide compounds can also be derived from monocyclic phenols, for example from phenol, resorcinol or hydroquinone; or they are based on polycyclic phenols, for example on bis(4-hydroxyphenyl)methane, 2,2-bis(4-hydroxyphenyl)propane, 2,2-bis(3,5-dibromo-4-hydroxyphenyl)propane, 4,4'-dehydroxydiphenyl sulfone or on condensation products of phenols with formaldehyde obtained under acid conditions, such as phenol novolaks.

Examples of other possible terminal epoxides are: glycidyl 1-naphthyl ether, glycidyl 2-phenylphenyl ether, 2-biphenyl glycidyl ether, N-(2,3-epoxypropyl)phthalimide and 2,3-epoxypropyl 4-methoxyphenyl ether.

III) N-Glycidyl compounds obtainable by dehydrochlorinating the products of the reaction of epichlorohydrin with amines, which contain at least one amino hydrogen atom. These amines are, for example, aniline, N-methylaniline, toluidine, n-butylamine, bis(4-aminophenyl)methane, m-xylylenediamine or bis(4-methylaminophenyl)methane, but also N,N,O-triglycidyl-m-aminophenol or N,N,O-triglycidyl-p-aminophenol.

However, the N-glycidyl compounds also include N,N'-di-, N,N',N''-tri- and N,N',N'',N'''-tetraglycidyl derivatives of cycloalkyleneureas, such as ethyleneurea or 1,3-propyleneurea, and N,N'-diglycidyl derivatives of hydantoins, such as of 5,5-dimethylhydantoin or glycol uril and triglycidyl isocyanurate.

IV) S-Glycidyl compounds, for example di-S-glycidyl derivatives derived from dithiols, for example ethane-1,2-dithiol or bis(4-mercaptomethylphenyl) ether.

V) Epoxide compounds containing a radical of the formula I' in which $R'_1$ and $R'_3$ together are —$CH_2$—$CH_2$—, and n' is 0, are bis(2,3-epoxycyclopentyl) ether, 2,3-epoxycyclopentyl glycidyl ether or 1,2-bis(2,3-epoxycyclopentoxy)ethane. An example of a terminal epoxy resin containing a radical of the formula I' in which $R'_1$ and $R'_3$ together are —$CH_2$—$CH_2$— and n' is 1 is 3',4'-epoxy-6'-methylcyclohexyl)methyl 3,4-epoxy-6-methylcyclohexanecarboxylate.

Examples of suitable terminal epoxides are:

a) liquid bisphenol A diglycidyl ethers, such as Araldit®GY 240, Araldit®(GY 250, Araldit®GY 260, Araldit®GY 266, Araldit®GY 2600, Araldit®MY 790;

b) solid bisphenol A diglycidyl ethers, such as Araldit®GT 6071, Araldit®GT 7071, Araldit®GT 7072, Araldit®GT 6063, Araldit®GT 7203, Araldit®GT 6064, Araldit®GT 7304, Araldit®GT 7004, Araldit®GT 6084, Araldit®GT 1999, Araldit®GT 7077, Araldit®GT 6097, Araldit®GT 7097, Araldit®GT 7008, Araldit®GT 6099, Araldit®GT 6608, Araldit®GT 6609, Araldit®GT 6610;

c) liquid bisphenol F diglycidyl ethers, such as Araldit®GY 281, Araldit®PY 302, Araldit®PY 306;

d) solid polyglycidyl ethers of tetraphenylethane, such as CG Epoxy Resin®0163;

e) solid and liquid polyglycidyl ethers of phenol-formaldehyde novolak, such as EPN 1138, EPN 1139, GY 1180, PY 307;

f) solid and liquid polyglycidyl ethers of o-cresol-formaldehyde novolak, such as ECN 1235, ECN 1273, ECN 1280, ECN 1299;

g) liquid glycidyl ethers of alcohols, such as Shell® glycidyl ether 162, Araldit®DY 0390, Araldit®DY 0391;

h) liquid glycidyl ethers of carboxylic acids, such as Shell®Cardura E terephthalates, trimellitates, Araldit®PY 284:

i) solid heterocyclic epoxy resins (triglycidyl isocyanurate), such as Araldit® PT 810;

j) liquid cycloaliphatic epoxy resins, such as Araldit®CY 179;

k) liquid N,N,O-triglycidyl ether of p-aminophenol, such as Araldit®MY 0510;

l) tetraglycidyl-4,4'-methylenebenzamine or N,N,N',N'-tetraglycidyldiaminophenylmethane, such as Araldit®MY 720, Araldit®MY 721.

Preference is given to the use of terminal epoxide compounds containing two functional groups. However, it is in principle also possible for terminal epoxide compounds containing one, two or more functional groups to be used. Predominantly employed are terminal epoxide compounds, in particular diglycidyl compounds, having aromatic structures.

If desired, a mixture of terminal epoxide compounds of different structures can also be employed.

Particularly preferred terminal epoxide compounds are diglycidyl ethers based on bisphenols, for example on 2,2-bis(4-hydroxyphenyl)propane (bisphenol A), bis(4-hydroxyphenyl)methane or mixtures of bis(ortho/para-hydroxyphenyl)methane (bisphenol F).

The terminal epoxide compounds can be employed in an amount of preferably at least 0.1 part for example from 0.1 to 50, preferably from 1 to 30 and in particular from 1 to 20 parts by weight, based on 100 parts by weight of PVC.

Perchlorate salts are, for example, compounds of the formula $M(ClO_4)_m$, where M is $NH_4^+$, $Na^+$, $K^+$, $Mg^{++}$, $Ca^{++}$, $Ba^{++}$ or $Al^{3+}$. The index m is 1, 2 or 3 corresponding to the valency of M.

The perchlorate salts can be employed in various customary administration forms, for example as a salt or aqueous solution adsorbed onto a support material, such as PVC, Ca silicate, zeolite or hydrotalcite, or bonded to a hydrotalcite by chemical reaction.

The perchlorate salts can be used in an amount of, for example, from 0.001 to 5, expediently from 0.01 to 3, particularly preferably from 0.01 to 2 parts by weight, based on 100 parts by weight of PVC.

The invention therefore preferably also relates to compositions additionally comprising, in addition to component a) and component b) (compound of the formula I containing at least one radical of the formula I), at least one Me(II) carboxylate and/or Me(II) phenoxide, where Me(II) is Ba, Ca, Mg or Zn.

In a further preference, the novel compositions comprise, in addition to component a) and component b), at least one Me(II) carboxylate, where Me(II) is Ba, Ca, Mg or Zn. Mixtures of barium/zinc or calcium/zinc carboxylates are particularly preferred as costabilizers here.

Preference is likewise given to compositions comprising, in addition to components a) and b), an epoxide compound or glycidyl compound and/or a phosphite and, if desired, an Me(II) carboxylate and/or Me(II) phenoxide.

Preference is furthermore given to compositions comprising, in addition to components a) and b), an epoxide compound or glycidyl compound and a perchlorate salt and/or a phosphite or phosphonite.

The known thermal stabilizers (for example carboxylates) can be present in the material to be stabilized in a concentration known to the person skilled in the art, for example in an amount of from 0.05 to 5% by weight Expedient compositions are those as described above in which component b) is present in an amount of from 0.05 to 5%, in particular from 0.1 to 5%, for example from 0.1 to 2%, based on the weight of component a).

Depending on the intended use of the polymers, further additives may also be incorporated before or during incorporation of the stabilizers; these further additives are, for example, antioxidants, lubricants (preferably montan wax or glycerol esters), fatty acid esters, paraffins, plasticizers, fillers, carbon black, asbestos, kaolin, talc, glass fibres, modifiers (for example impact additives), optical brighteners, pigments, light stabilizers, UV absorbers, flameproofing agents, processing auxiliaries or antistatics. Particular preference is given to light stabilizers having a hindered amine structure, as defined, for example, in EP-A-421 933.

Furthermore other possible additives are β-aminocrotonates, for example the compounds described in DE-A-804 442, DE-A-807 207 and JP-A-75/17454, pyrroles, for example the compounds indicated in EP-A-22 087, polyols, for example the compounds described in DE-A-3 019 910, β-diketones, for example the compounds indicated in DE-A-2 600 516, or alternatively mixtures of β-diketones and hydrotalcites, as described, for example, in EP-A-63 180.

Preference is given to compositions comprising, in addition to components a) and b), lubricants, pigments, modifiers, processing auxiliaries, fillers, antioxidants and/or light stabilizers.

If plasticizers, in particular organic plasticizers, are present in the novel compositions, those from the following groups, for example, are suitable.

A) Phthalates (esters of phthalic acid)

Examples of these plasticizers are dimethyl, diethyl, dibutyl, dihexyl, di-2-ethylhexyl, di-n-octyl, di-isooctyl, di-isononyl, di-isodecyl, di-isotridecyl, dicyclohexyl, dimethylcyclohexyl, dimethyl glycol, dibutyl glycol, benzyl butyl and diphenyl phthalates, and mixtures of phthalates, such as $C_7$–$C_9$- and $C_9$–$C_{11}$alkyl phthalates made from predominantly linear alcohols, $C_6$–$C_{10}$-n-alkyl phthalates and $C_8$–$C_{10}$-n-alkyl phthalates. From these, preference is given to dibutyl, dihexyl, di-2-ethylhexyl, di-n-octyl, di-isooctyl, di-isononyl, di-isodecyl, di-isotridecyl and benzyl butyl phthalates, and said mixtures of alkyl phthalates. Particular preference is given to di-2-ethylhexyl phthalate (DOP).

B) Esters of aliphatic dicarboxylic acids, in particular esters of adipic, azelaic and sebacic acids.

Examples of these plasticizers are di-2-ethylhexyl adipate, di-isooctyl adipate (mixture), di-isononyl adipate (mixture), di-isodecyl adipate (mixture), benzyl butyl adipate, benzyl octyl adipate, di-2-ethylhexyl azelate, di-2-ethylhexyl sebacate and di-isodecyl sebacate (mixture). Preference is given to di-2-ethylhexyl adipate and di-isooctyl adipate.

C) Esters of trimellitic acid, for example tri-2-ethylhexyl trimellitate, tri-isodecyl trimellitate (mixture), tri-isotridecyl trimellitate, tri-isooctyl trimellitate (mixture) and tri-$C_6$–$C_8$alkyl, tri-$C_6$–$C_{10}$alkyl, tri-$C_7$–$C_9$alkyl and tri-$C_9$–$C_{11}$ alkyl trimellitates. The last-mentioned trimellitates are formed by esterifying trimellitic acid by means of the appropriate alkanol mixtures. Preferred tri-mellitates are tri-2-ethylhexyl trimellitate and said trimellitates made from alkanol mixtures.

D) Polymer plasticizers

A definition of these plasticizers and examples thereof are given in "Plastics Additives Handbook", edited by H. G achter and H. Müller, Hanser Publishers, 1985, page 284, chapter 5.7.10, and in "PVC Technology", edited by W. V. Titow, 4th Ed., Elsevier Publ., 1984, pages 165–170. The most usual starting materials for the preparation of polyester plasticizers are: dicarboxylic acids, such as adipic, phthalic, azelaic and sebacic acids; diols, such as 1,2-propanediol, 1,3-butanediol, 1,4-butanediol, 1,6-hexanediol, neopentyl glycol and diethylene glycol; monocarboxylic acids, such as acetic, caproic, caprylic, lauric, myristic, palmitic, stearic, pelargonic and benzoic acids; monofunctional alcohols, such as isooctanol, 2-ethylhexanol, isodecanol and $C_7$–$C_9$alkanol and $C_9$–$C_{11}$alkanol mixtures. Particularly advantageous are polyester plasticizers made from said dicarboxylic acids and monofunctional alcohols.

E) Esters of phosphoric acid,

A definition of these esters is given in the abovementioned "Plastics Additives Handbook" on page 271, chapter 5.7.2. Examples of these phosphates are tributyl phosphate, tri-2-ethylbutyl phosphate, tri-2-ethylhexyl phosphate, trichloroethyl phosphate, 2-ethylhexyl diphenyl phosphate, cresyl diphenyl phosphate, triphenyl phosphate, tricresyl phosphate and trixylenyl phosphate. Preference is given to tri-2-ethylhexyl phosphate.

F) Chlorinated hydrocarbons (paraffins)

G) Hydrocarbons

H) Monoesters, for example butyl oleate, phenoxyethyl oleate, tetrahydrofurfuryl oleate and esters of alkylsulfonic acids.

I) Glycol esters, for example diglycol benzoates.

Definitions and examples of plasticizers from groups F) to I) are given in the following handbooks:

"Plastics Additives Handbook", edited by H. Gächter and H. Müller, Hanser Publishers, 1985, page 284, chapter 5.7.11 (Group F)) and chapter 5.7.13 (Group G)).

"PVC Technology", edited by W. V. Titow, 4th Ed., Elsevier Publishers, 1984, pages 171–173, chapter 6.10.2 (Group F)), page 174, chapter 6.10.5 (group G)), page 173, chapter 6.10.3 (group H)) and pages 173–174, chapter 6.10.4 (group I)).

Particular preference is given to plasticizers from groups A) to E), in particular A) to C) especially the plasticizers in these groups which have been mentioned as preferred. Di-2-ethyl-hexyl phthalate (DOP) is particularly favourable.

The plasticizers can be used in an amount of, for example, from 15 to 70, expediently from 15 to 60, in particular from 20 to 50 parts by weight, based on 100 parts by weight of polymer composition.

The novel compositions may also comprise further stabilizers which are conventional for chlorine-containing polymers.

The novel compositions may furthermore comprise conventional antioxidants, light stabilizers and UV absorbers. Examples of these are the following:

1. Antioxidants 1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol, and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-di-tert-butyl-4-methoxyphenol, 2,5-di-tert-butyl-hydroquinone, 2,5-di-tert-amyl-hydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Hydroxylated diphenyl thioethers, for example 2,2'-thiobis(6-tert-butyl-4-methylphenol), 2,2'-thiobis(4-octylphenol), 4,4'-thiobis(6-tert-butyl-3-methylphenol), 4,4'-thio-bis(6-tert-butyl-2-methylphenol), 4,4'-thiobis(3,6-di-sec-amylphenol), 4,4'-bis(2,6-dimethyl-4-hydroxyphenyl) disulfide.

1.5. Alkylidenebisphenols, for example 2,2'-methylene-bis(6-tert-butyl-4-methylphenol), 2,2'-methylene-bis(6-tert-butyl-4-ethylphenol), 2,2'-methylene-bis[4-methyl-6-(α-methylcyclohexyl)phenol], 2,2'-methylene-bis(4-methyl-6-cyclohexylphenol), 2,2'-methylene-bis(6-nonyl-4-methylphenol), 2,2'-methylene-bis(4,6-di-tert-butylphenol), 2,2'-ethylidene-bis(4,6-di-tert-butylphenol), 2,2'-ethylidene-bis(6-tert-butyl-4-isobutylphenol), 2,2'-methylene-bis[6-(α-methylbenzyl)-4-nonylphenol], 2,2'-methylene-bis[6-(α,α-dimethylbenzyl)-4-nonylphenol], 4,4'-methylene-bis(2,6-di-tert-butylphenol), 4,4'-methylene-bis-(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methylphenyl) dicyclopentadiene, bis[2-(3'-tert-butyl-2'-hydroxy-5'-methylbenzyl)-6-tert-butyl-4-methyl-phenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.6. O-, N- and S-benzyl compounds, for example 3,5,3',5'-tetra-tert-butyl-4,4-dihydroxydibenzyl ether, octadecyl 4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide, isooctyl 3,5-di-tert-butyl-4-hydroxybenzylmercaptoacetate.

1.7. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl) malonate, didodecylmercaptoethyl 2,2-bis(3,5-di-tert-butyl-4-hydroxybenzyl)malonate, di[4-(1,1,3,3-tetramethylbutyl) phenyl]2,2-bis(3,5-di-tert-butylhydroxybenzyl)-malonate.

1.8. Hydroxybenzyl aromatic compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butylhydroxyphenylpropionyl)hexahydro-1,3,5-triazine, 1,3,5-tris(3,5-dicyclohexyl-4-hydroxybenzyl) isocyanurate.

1.10. Benzylphosphonates, for example dimethyl 2,5-di-tert-butylhydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of monoethyl 3,5-di-tert-butyl-4-hydroxybenzyl phosphonate.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl) propionic acid with monohydric or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.13. Esters of β-(5-tert-butyl-4-hydroxy-3-methylphenyl)propionic acid with monohydric or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.14. Esters of β-(3,5-dicyclohexyl-4-hydroxyphenyl) propionic acid with monohydric or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.15. Esters of 3,5-di-tert-butyl-4-hydroxyphenylacetic acid with monohydric or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol pentaerythritol, tri(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.16. Amides of β-(3,5-di-tert-butyl-4-hydroxyphenyl) propionic acid, for example N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3- tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazol-2-yl phenol]; transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$ where R=3'-tert-butyl-4'-hydroxy-5'-2H-benzotriazol-2-yl phenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of unsubstituted or substituted benzoic acids, for example 4-tert-butyl-phenyl salicylate, phenyl salicylate, octylphenyl salicylate, dibenzoylresorcinol, bis(4-tert-butyl-benzoyl)resorcinol, benzoylresorcinol, 2,4-di-tert-butylphenyl 3,5-di-tert-butylhydroxy-benzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the product of the condensation of 1-hydroxyethyl-2,2,6,6-tetramethyl-4-hydroxypiperidine and succinic acid, the product of the condensation of N,N'-bis(2,2,6,6-tetramethyl-4-piperidyl)hexamethylenediamine and 4-tert-octylamino-2,6-dichloro-1,3,5-s-triazine, tris-(2, 2,6,6-tetramethyl-4-piperidyl) nitrilotriacetate, tetrakis(2,2, 6,6-tetramethyl-4-piperidyl) 1,2,3,4-butanetetraoate, 1,1'-(1, 2-ethanediyl)bis-(3,3,5,5-tetramethylpiperazinone), 4-benzoyl-2,2,6,6-tetramethylpiperidine, 4-stearyloxy-2,2, 6,6-tetramethylpiperidine, bis-(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the product of the condensation of N,N'-bis(2,2,6,6-tetramethyl-4-piperidyl) hexamethylene diamine and 4-morpholino-2,6-dichloro-1,3, 5-triazine, the product of the condensation of 2-chloro-4,6-di(4n-butylamino-2,2,6,6-tetramethyl- piperidyl)1,3,5-triazine and 1,2-bis(3-aminopropylamino)ethane, the product of the condensation of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2, 4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione.

2.5. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butoxypropoxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine.

The novel compositions can be prepared in a manner known per se. In general, the stabilizer system is incorporated into the polymer, to which end equipments known per se, such as calenders, mixers, compounders and the like, are appropriate.

The incorporation of the stabilizer components into the chlorine-containing polymer is best carried out, in a conventional manner, on mixing rolls, for example in a 2-roll mill, at temperatures of from 150° to 200° C. In general, adequate homogenization can be achieved within from 5 to 15 minutes. The components can be added individually or together as a premix. A liquid premix has proved expedient, ie. the operation is carried out in the presence of inert solvents and/or plasticizers.

The compositions stabilized in accordance with the present invention can be converted into the desired form in a known manner. Such methods are, for example, grinding, calendering, extrusion and injection moulding, furthermore extrusion blow- moulding or processing by the plastisol method. The compositions can also be converted into foams.

Preferred stabilized chlorine-containing polymer compositions are unplasticized or plasticizer-free or essentially plasticizer-free compositions.

The novel compositions are particularly suitable, in the form of rigid formulations, for hollow articles (bottles), packaging films (thermoformed films), blown films, crash-pad films (automobile), tubes, roof sheeting, foams, heavy profiles (window frames), light-wall profiles, building profiles, sidings, fittings, office films and equipment housings (computers and domestic appliances).

Other compositions, in the form of flexible formulations, are suitable for wire sheaths, cable insulations, decorative films, roof sheeting, foams, agricultural sheeting, tubes, sealing profiles, office films, sheeting for inflated tents and films for motor vehicle interiors.

Examples of the use of the novel compositions as plastisols are artificial leather, floor coverings, textile coatings, wall coverings, coil coatings and motor vehicle underseal.

Examples of sintered PVC applications of the novel compositions are slush, slush mould and coil coatings.

The polymer compositions described above are preferably used for the production of rigid profiles for external applications and for the production of rigid sheeting.

The invention furthermore relates to the use of at least one compound containing at least one radical of the formula I as stabilizer for chlorine-containing polymers against oxidative, thermal or light-induced degradation.

The present invention also relates to a process for stabilizing a chlorine-containing polymer against oxidative, thermal or light-induced degradation, which comprises incorporating or applying at least one compound containing at least one radical of the formula I into or to this polymer.

The preferred compounds containing at least one radical of the formula I for use as stabilizers and the stabilization process are the same as described for the composition comprising a chlorine-containing polymer.

The invention likewise relates to novel compounds of the formula II

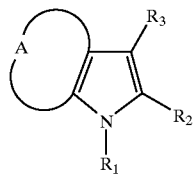
(II)

in which

A is a group of the formula III or IV

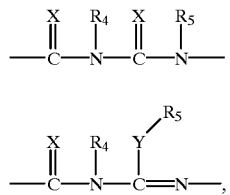
(III)

(IV)

X is oxygen or sulfur,

Y is oxygen, sulfur or

$R_1$ is hydrogen, $C_1$–$C_{12}$alkyl, $C_2$–$C_{12}$alkyl which is interrupted by oxygen, sulfur or carboxyl; hydroxyl-substituted $C_1$–$C_{12}$alkyl; $C_3$–$C_6$alkenyl, $C_5$–$C_8$cycloalkyl which is unsubstituted or substituted by one to three $R_6$ radicals; phenyl which is unsubstituted or substituted by one to three $R_6$ radicals; $C_7$–$C_9$phenylalkyl which is unsubstituted or substituted on the phenyl ring by one to three $R_6$ radicals; an alkali metal or an alkaline earth metal, $R_2$ and $R_3$, independently of one another, are hydrogen, $C_1$–$C_{12}$alkyl, $C_2$–$C_{12}$alkyl which is interrupted by oxygen, sulfur or carboxyl; hydroxyl-substituted $C_1$–$C_{12}$alkyl; $C_3$–$C_6$alkenyl, $C_5$–$C_8$cycloalkyl which is unsubstituted or substituted by one to three $R_6$ radicals; phenyl which is unsubstituted or substituted by one to three $R_6$ radicals; $C_7$–$C_9$-phenylalkyl which is unsubstituted or substituted on the phenyl ring by one to three $R_6$ radicals;

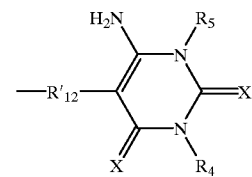

or a radical of the formula V or VI

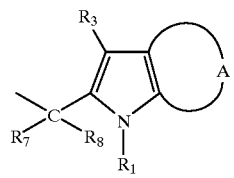
(V)

(VI)

in which A and $R_1$ are as defined above, or furthermore one of the radicals $R_2$ and $R_3$ is hydroxyl, formyl, $C_1$–$C_{12}$alkoxy, phenoxy which is unsubstituted or substituted by one to three $R_6$ radicals; $C_1$–$C_{12}$alkanoyloxy, benzoyloxy which is unsubstituted or substituted by one to three $R_6$ radicals;

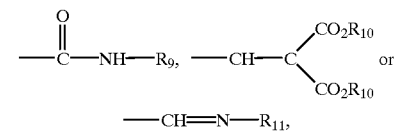

$R_4$ and $R_5$, independently of one another, are hydrogen, $C_1$–$C_{12}$alkyl, $C_2$–$C_{12}$alkyl which is interrupted by oxygen, sulfur or carboxyl; hydroxyl-substituted $C_1$–$C_{12}$alkyl; $C_3$–$C_6$-alkenyl, $C_5$–$C_8$cycloalkyl which is unsubstituted or substituted by one to three $R_6$ radicals; phenyl which is unsubstituted or substituted by one to three $R_6$ radicals; or $C_7$–$C_9$phenylalkyl which is unsubstituted or substituted on the phenyl ring by one to three $R_6$ radicals, $R_6$ is $C_1$–$C_4$alkyl, $C_1$–$C_4$alkoxy, $C_5$–$C_8$cycloalkyl, hydroxyl or chlorine, $R_7$ and $R_8$, independently of one another, are hydrogen, $CF_3$, $C_1$–$C_{12}$alkyl, phenyl or $C_7$–$C_9$phenylalkyl, or $R_7$ and $R_8$, together with the carbon atom to which they are bonded, form an unsubstituted or $C_1$–$C_4$alkyl-substituted $C_5$–$C_{12}$cycloalkylidene ring, $R_9$ is phenyl which is unsubstituted or substituted by one to three $R_6$ radicals;

$R_{10}$ is hydrogen, $C_1$–$C_{12}$alkyl, $C_2$–$C_{12}$alkyl which is interrupted by oxygen or sulfur, hydroxyl-substituted $C_1$–$C_{12}$alkyl; $C_3$–$C_6$alkenyl, $C_5$–$C_8$cycloalkyl which is unsubstituted or substituted by one to three $R_6$ radicals; phenyl which is unsubstituted or substituted by one to three $R_6$ radicals; or $C_7$–$C_9$phenylalkyl which is unsubstituted or substituted on the phenyl ring by one to three $R_6$ radicals, $R_{11}$ is $C_1-C_{12}$alkyl, $C_2-C_{12}$alkyl which is interrupted by oxygen or sulfur; hydroxyl-substituted $C_1-C_{12}$alkyl; $C_3-C_6$alkenyl, $C_5-C_8$cycloalkyl which is unsubstituted or substituted by one to three $R_6$ radicals; phenyl which is unsubstituted or substituted by one to three $R_6$ radicals; or $C_7-C_9$-phenylalkyl which is unsubstituted or substituted on the phenyl ring by one to three $R_6$ radicals, $R'_{12}$ is a direct bond or

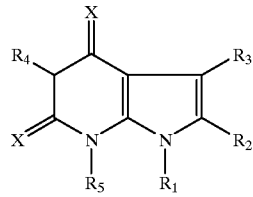

and $R'_{13}$ is hydrogen or $C_1-C_8$alkyl; with the exception of the compounds of the formula VII

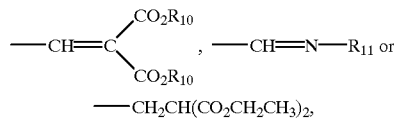

(VII)

in which

X is oxygen, $R_1$ is hydrogen, methyl or phenyl, $R_2$ is hydrogen, hydroxyl, formyl, $C_1-C_3$alkyl, phenyl, 4-chlorophenyl,

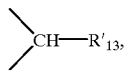

$R_3$ is hydrogen, hydroxyl, formyl, $C_1-C_5$alkyl, phenyl or —$CH_2CO_2R_{10}$, $R_4$ and $R_5$, independently of one another, are hydrogen, $C_1-C_4$alkyl, alkyl, phenyl, 4-methylphenyl or benzyl, $R_{10}$ is $C_1-C_4$alkyl, $R_{11}$ is methyl, alkyl, benzyl or phenyl, and with the exception of the compound (152)

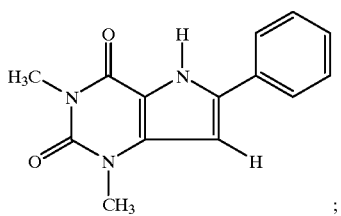

(152)

however, with the compounds

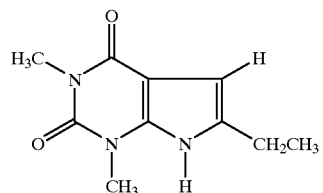

and

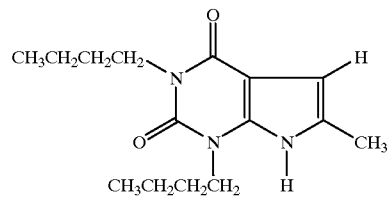

not being excluded.

Preferred groups of novel compounds of formula II correspond to those in the preferences expressed above for the novel compositions.

Of particular interest are compounds of the formula II in which the compound of the formula II is a compound of the formula VII, VIIa or VIII

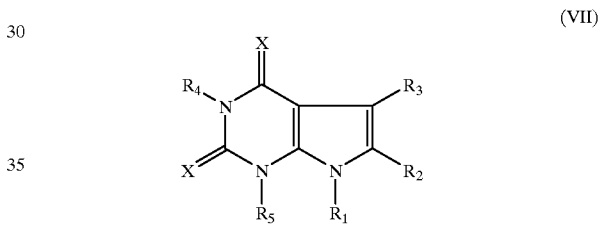

(VII)

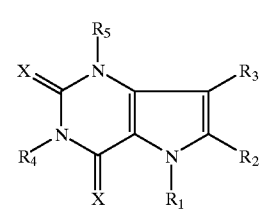

(VIIa)

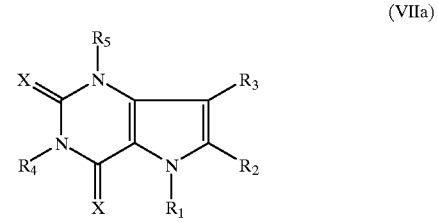

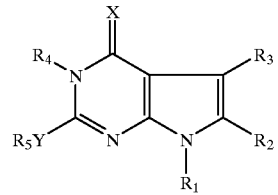

(VIII)

in which

X is oxygen or sulfur,

Y is oxygen, sulfur or

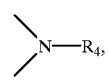

$R_1$ is hydrogen, $C_1-C_{10}$alkyl, $C_2-C_{12}$alkyl which is interrupted by oxygen; hydroxyl-substituted $C_1-C_{10}$alkyl;

$C_3$–$C_6$alkenyl, $C_5$–$C_8$cycloalkyl, phenyl. $C_7$–$C_9$phenylalkyl, an alkali metal or an alkaline earth metal, $R_2$ and $R_3$, independently of one another, are hydrogen, $C_1$–$C_{10}$alkyl, $C_2$–$C_{12}$alkyl which is interrupted by oxygen; hydroxyl-substituted $C_1$–$C_{10}$alkyl; $C_3$–$C_6$alkenyl, $C_5$–$C_8$cycloalkyl, phenyl, $C_7$–$C_9$phenylalkyl which is unsubstituted or substituted on the phenyl ring by one to three $R_6$ radicals;

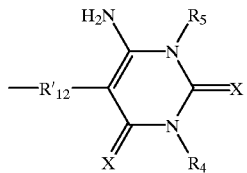

or a radical of the formula IX, X, XI or XII

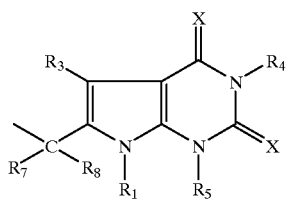
(IX)

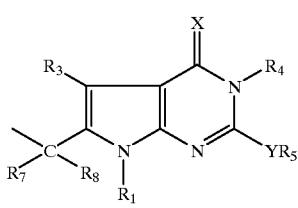
(X)

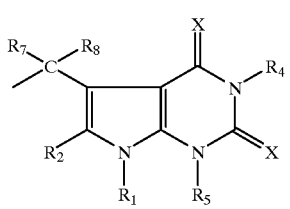
(XI)

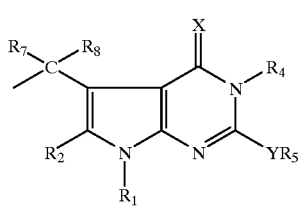
(XII)

in which X, Y, $R_1$, $R_2$ and $R_3$ are as defined above, or furthermore one of the radicals $R_2$ and $R_3$ is hydroxyl, formyl, $C_1$–$C_{10}$alkoxy, phenoxy, $C_1$–$C_{10}$alkanoyloxy, benzoyloxy,

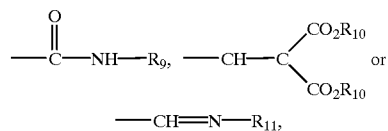

$R_4$ and $R_5$, independently of one another, are hydrogen, $C_1$–$C_{10}$alkyl, $C_2$–$C_{12}$alkyl which is interrupted by oxygen; hydroxyl-substituted $C_1$–$C_{10}$alkyl; $C_3$–$C_6$alkenyl, $C_5$–$C_8$cycloalkyl, phenyl or $C_7$–$C_9$phenylalkyl, $R_6$ is $C_1$–$C_4$alkyl, $C_1$–$C_4$alkoxy, cyclohexyl, hydroxyl or chlorine, $R_7$ and $R_8$, independently of one another, are hydrogen, $C_1$–$C_{10}$alkyl, phenyl or $C_7$–$C_9$-phenylalkyl, $R_9$ is phenyl, $R_{10}$ is $C_1$–$C_{10}$alkyl, $C_2$–$C_{12}$alkyl which is interrupted by oxygen; $C_3$–$C_6$alkenyl, $C_5$–$C_8$-cycloalkyl, phenyl or $C_7$–$C_9$phenylalkyl, $R_{11}$ is $C_1$–$C_{10}$alkyl, $C_5$–$C_8$cycloalkyl, phenyl or $C_7$–$C_9$phenylalkyl, $R'_{12}$ is a direct bond or

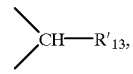

and $R'_{13}$ is hydrogen or $C_1$–$C_4$alkyl.

Preference is given to compounds of the formula II in which $R_4$ and $R_5$, independently of one another, are hydrogen or $C_1$–$C_4$alkyl.

Especial preference is given to compounds of the formula II in which

X and Y are oxygen, $R_1$ is hydrogen, 2-hydroxyethyl, sodium, magnesium or calcium, $R_2$ is hydrogen, $C_1$–$C_4$alkyl, phenyl, 2,6-di-tert-butyl-4-hydroxybenzyl, hydroxyl,

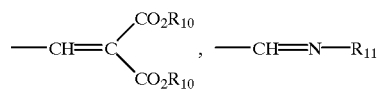

or a radical of the formula IX

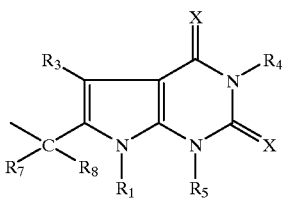
(IX)

in which X and $R_1$ are as defined above, $R_3$ is hydrogen, hydroxyl, $C_1$–$C_4$alkyl, phenyl,

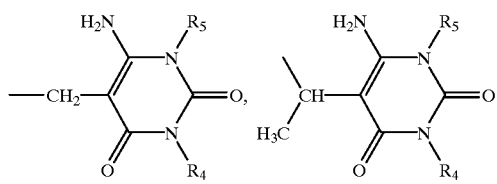

or 2,6-di-tert-butyl-4-hydroxybenzyl, $R_4$ and $R_5$, independently of one another, are hydrogen or $C_1$–$C_4$alkyl, $R_7$ and $R_8$, independently of one another, are hydrogen, $C_1$–$C_9$alkyl or phenyl, $R_{10}$ is $C_1$–$C_4$alkyl, and $R_{11}$ is benzyl.

Some of the compounds containing at least one radical of the formula I and some of the compounds of the formula II are known, and their preparation is described, for example, in the following publications: N. M. Smirnova, L. F. Linberg, V. M. Nesterov and T. S. Safanova, Chemistry of Heterocyclic Compounds 1978, 443–446; H. Ogura, M. Sakaguchi and K. Takeda, Chem. Pharm. Bull. 20 (2), 404–408 (1972); S. Senda and K. Hirota, Chem. Pharm. Bull. 22 (12), 2921–28 (1974); S. Senda and K. Hirota, Chem. Pharm. Bull. 22 (7), 1459–1467 (1974); F. Yoneda, M. Higuchi K. Senga, M. Kanohori and S. Nishigaki, Chem. Pharm. Bull. 21 (3), 473–477 (1973); or K. Hirota et al., Synthesis 1982, 1097–1099. The novel compounds containing at least one radical of the formula I and the compounds of the formula II can be prepared analogously to the literature procedures mentioned above.

However, these known methods do not always give the desired novel stabilizers in good yields.

The invention therefore furthermore relates to a novel process for the preparation of compounds of the formula XIII or XIV (XIII)

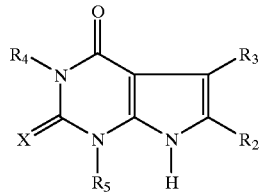

(XIV)

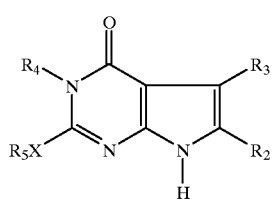

in which the general symbols are as defined under the formula II, which comprises reacting a compound of the formula XV or XVI (XV)

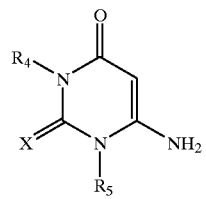

(XVI)

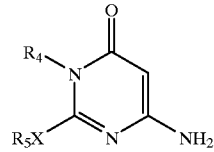

in which the general symbols are as defined under the formula II, with a compound of the formula XVIIa, XVIIb, XVIIc, XVIId, XVIIe or XVIIf (XVIIa)

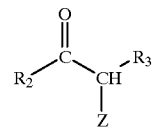

(XVIIb)

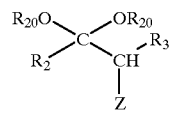

(XVIIc)

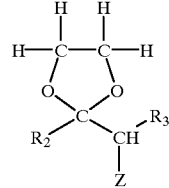

(XVIId)

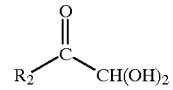

(XVIIe)

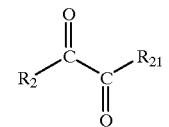

(XVIIf)

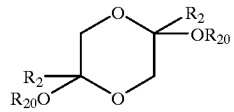

in which $R_2$ and $R_3$ are as defined under the formula II, $R_{20}$ is $C_1$–$C_4$alkyl, $R_{21}$ is $C_1$–$C_4$-alkyl, and Z is a leaving group, in the presence of an ammonium salt.

$C_1$–$C_4$alkyl $R_{20}$ and $R_{21}$ are, for example, methyl, ethyl, propyl, isopropyl, n-butyl, sec-butyl, isobutyl or tert-butyl. Particularly preferred meanings of $R_{20}$ and $R_{21}$ are methyl and butyl.

The reaction is preferably carried out in the presence of a solvent. Suitable solvents for carrying out the reaction are both protic and dipolar aprotic solvents.

Particularly suitable protic solvents are alcohols (for example methanol, ethanol, propanol or isopropanol), ketones (for example acetone or methyl ethyl ketone), ethers (for example tetrahydrofuran, dioxane, diethylene glycol or 2-methoxyethanol) and carboxylic acids (for example acetic acid), which can be mixed with water in any desired ratio. The novel process is preferably carried out in an aqueous solvent, in particular aqueous acetic acid or only in water.

Particularly suitable dipolar aprotic solvents are those which can be mixed with water in any desired ratio, for example acetonitrile, dimethylformamide, dimethylacetamide, dimethyl sulfoxide or N-methylpyrrolidone.

The reaction is preferably carried out at elevated temperature, in particular in the temperature range from 40 to 160° C. An especially preferred temperature range is from 40 to 140° C., especially from 60 to 120° C.

In the reaction of the compound of the formula XV or XVI with the compound of the formula XVIIa, XVIIb or XVIIc, the compound of the formula XVIIa, XVIIb or XVIIc is preferably employed in a stoichiometric amount or in excess with respect to the employed compound of the formula XV or XVI. Of interest is an excess of from 1.1 to 4 equivalents, in particular from 1.1 to 3.0 equivalents, relative to the employed compound of the formula XV or XVI. A very particularly preferred reactant ratio is from 1.0 to 1.5.

The leaving group Z in the compounds of the formula XVIIa, XVIIb and XVIIc is, for example, halogen, hydroxyl or

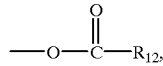

in which $R_{12}$ is hydrogen, $C_1$–$C_4$alkyl or unsubstituted or $R_{13}$-substituted phenyl; and $R_{13}$ is halogen, nitro, $CF_3$, $C_1$–$C_4$alkyl or $C_1$–$C_4$alkoxy.

Halogen is, for example, chlorine, bromine or iodine. Chlorine or bromine, in particular chlorine, is of particular interest.

$C_1$–$C_4$alkyl $R_{12}$ is a branched or unbranched radical, for example methyl, ethyl, propyl, isopropyl, n-butyl, sec-butyl, isobutyl or tert-butyl. $R_{12}$ is preferably methyl.

Unsubstituted or $R_{13}$-substituted phenyl $R_{12}$ is, for example, phenyl, p-nitrophenyl, p-chlorophenyl, p-methylphenyl, p-methoxyphenyl or p-trifluoromethylphenyl.

Preferred ammonium salts for the novel process are compounds of the formula XVIII

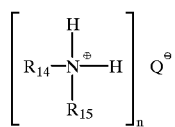

(XVIII)

in which n is 1 or 2, $R_{14}$ and $R_{15}$, independently of one another, are hydrogen, $C_1$–$C_{12}$alkyl, $C_2$–$C_{12}$alkyl which is interrupted by oxygen or sulfur; hydroxyl-substituted $C_1$–$C_{12}$alkyl; $C_3$–$C_6$alkenyl, $C_5$–$C_8$cycloalkyl which is unsubstituted or substituted by one to three $R_{16}$ radicals; phenyl which is unsubstituted or substituted by one to three $R_{16}$ radicals; $C_7$–$C_9$phenylalkyl which is unsubstituted or substituted on the phenyl ring by one to three $R_{16}$ radicals; or $R_{14}$ and $R_{15}$, together with the nitrogen atom to which they are bonded, form a $C_4$–$C_7$cycloalkylene ring, which may additionally be interrupted by oxygen or sulfur, $R_{16}$ is $C_1$–$C_4$alkyl, $C_1$–$C_4$alkoxy, $C_5$–$C_8$cycloalkyl, hydroxyl or chlorine, and if n=1, $Q^\ominus$ is

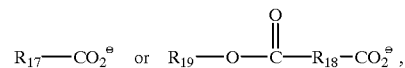

and
if n=2, $Q^\ominus$ is carbonate or $^\ominus O_2C$—$R_{18}$—$CO_2^\ominus$, $R_{17}$ is hydrogen, hydroxyl, $C_1$–$C_{18}$alkyl, phenyl or benzyl, $R_{18}$ is a direct bond or $C_1$–$C_6$alkylene, and $R_{19}$ is hydrogen or $C_1$–$C_{18}$alkyl.

Especially preferred ammonium salts for the novel process are, for example, ammonium formate, ammonium acetate, ammonium propionate, methylammonium acetate, ethylammonium acetate, n-propylammonium acetate, n-butylammonium acetate, 2-hydroxyethylammonium acetate, dimethylammonium acetate, diethylammonium acetate, di-n-butylammonium acetate, ammonium carbonate, ammonium hydrogencarbonate, ammoniumoxalate, ammonium malonate and ammonium adipate. Of particular interest are ammonium acetate and di-n-butylammonium acetate.

The ammonium salt required for the novel process can be employed in any desired molar ratio, ie. in an excess or a substoichiometric amount, relative to the compound of the formula XV or XVI. Of interest is an amount of ammonium salt of from 0.1 to 3 equivalents, in particular from 0.25 to 1.5 equivalents, relative to the employed compound of the formula XV or XVI.

The products from the novel process are preferably isolated by filtration of the precipitated products. The resultant filtrate or the mother liquor can be re-used as starting material for a further reaction in the novel process.

The present invention therefore also relates to a process in which, when the reaction is complete, a mixture comprising a precipitate of the compound of the formula XIII or XIV and a mother liquor is formed, and the mother liquor is separated from the precipitate and used as reaction medium in a further reaction in accordance with the novel process mentioned above.

Some of the compounds of the formulae XV and XVI are known or can be prepared analogously to N. M. Smirnova, L. F. Linberg, V. M. Nesterov and T. S. Safanova, Chemistry of Heterocyclic Compounds 1978, 443–446; H. Ogura, M. Sakaguchi and K. Takeda, Chem. Pharm. Bull. 20 (2), 404–408 (1972); S. Senda and K. Hirota, Chem. Pharm. Bull. 22 (12), 2921–28 (1974); S. Senda and K. Hirota, Chem. Pharm. Bull. 22 (7), 1459–1467 (1974); or F. Yoneda, M. Higuchi, K. Senga, M. Kanohori and S. Nishigaki, Chem. Pharm. Bull. 21 (3), 473–477 (1973).

Preferred compounds of the formulae XVIIa, XVIIb, XVIIc, XVIId, XVIIe and XVIIf are, for example, glyoxal, methylglyoxal, phenylglyoxal, diacetyl, 2,3-hexanedione, 3,4-hexanedione, ethyl diethoxyacetate, hydroxyacetone, hydroxy-3,3-dimethylbutanone, 3-hydroxy-2-butanone, ω-hydroxyacetophenone, 2,5-dimethyl-2,5-dimethoxy-1,4-dioxane, chloroacetone, phenacyl chloride, phenacyl bromide, 1-chloro-3,3-dimethyl-2-butanone, α-bromopropiophenone, chloroacetaldehyde and bromoacetaldehyde, and the methyl and ethyl acetals thereof; and acetoxyacetone. These compounds are known from the literature or commercially available from Fluka or Aldrich.

The compounds of the formula VII or VIII in which $R_2$ is a radical of the formula IX or X and/or $R_3$ is a radical of the formula XI or XII are preferably prepared starting from the compounds of the formula XIII or XIV in which $R_2$ and/or $R_3$ is hydrogen prepared by the novel process outlined above, by reaction with a compound of the formula XIX

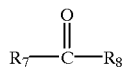
(XIX)

in which $R_7$ and $R_8$ are as defined above.

If the compound of the formula XIX is an aldehyde, the reaction is preferably carried out in refluxing aqueous formic acid, acetic acid or propionic acid. If the compound of the formula XIX is a ketone, the reaction is preferably carried out in a mixture of aqueous hydroiodic acid and acetic anhydride in a temperature range from 20 to 60° C., in particular from 30 to 50° C.

Preferred compounds of the formula XIX are, for example, formaldehyde, acetaldehyde, propionaldehyde, benzaldehyde, acetone, methyl ethyl ketone, di-n-butyl ketone, methyl nonyl ketone, acetophenone, cyclopentanone, cyclohexanone and 5-methyl-2-hexanone.

The examples below illustrate the invention in greater detail. Parts and percentages are by weight.

EXAMPLE 1

Preparation of Compound (101) (Table 1)

The preparation can be carried out analogously to the process described by N. M. Smirnova, L. F. Linberg, V. M. Nesterov and T. S. Safanova, Chemistry of Heterocyclic Compounds 1978, 443–446.

A mixture of 23.1 g (0.10 mol) of 1,3-dimethyl-5-chloroacetyl-4-aminouracil, 14.2 g (0.10 mol) of potassium carbonate and 250 ml of dioxane is refluxed with stirring for 14 hours. The reaction mixture is cooled, diluted with 300 ml of water, evaporated to a volume of 130 ml in a vacuum rotary evaporator, and cooled to 10° C. The crystals which precipitate are filtered off, washed with 2×80 ml of water and dried, giving 13.0 g (61%) of compound (101) (Table 1), orange crystals, m.p. 228–232° C.

EXAMPLE 2

Preparation of Compound (102) (Table 1)

The preparation can be carried out analogously to the process described by H. Ogura, M. Sakaguchi and K. Takeda, Chem. Pharm. Bull. 20 (2), 404–408 (1972).

A mixture of 16.7 g (0.10 mol) of ethyl bromoacetate, 15.5 g of (0.10 mol) of 4-amino-1,3-dimethyluracil and 100 ml of dimethylformamide is refluxed with siring for 4 hours. The reaction mixture is then left to stand at room temperature for 48 hours. The crystals are filtered off, washed with ether and dried. Crystallization from n-butanol gives 13.4 g (72%) of compound (102) (Table 1), red crystals, m.p. 310° C.

EXAMPLE 3

Preparation of Compound (103) (Table 1)

A mixture of 155.2 g (1.0 mol) of 4-amino-1,3-dimethyluracil, 101.8 g (1.1 mol) of chloroacetone, 154.2 g (2.0 mol) of ammonium acetate and 1200 ml of water are refluxed with stirring for 14 hours. The mixture is cooled to 10° C., and the precipitate is filtered off with suction, washed twice with 100 ml of water and dried to constant weight, giving 106 g (55%) of compound (103) (Table 1), yellow crystals, m.p. 313–314° C. The mother liquor can be re-used a number of times. The yield then increases to 60% of theory on use of the same molar amounts of starting materials.

EXAMPLE 4

Preparation of Compound (104) (Table 1)

The preparation is carried out analogously to the process described by S. Senda and K. Hirota, Chem. Pharm. Bull. 22 (12), 2921–28 (1974).

5.4 g (0.05 mol) of benzylamine are added to a suspension of 13.5 g (0.05 mol) of 6-dimethylmethylene(1,3-dimethyl-2,4-dioxo-1,2,3,4-tetrahydropyrrolo[2,3-d]pyrimidine) ammonium chloride [S. Senda and K. Hirota, Chem. Pharm. Bull. 22 (12), page 2924 (1974), compound 2a] and 100 ml of absolute ethanol. The reaction mixture is stirred at 25° C. for 30 minutes and then evaporated in a vacuum rotary evaporator, and 200 ml of water are added to the residue. The insoluble material is filtered off and dried. Crystallization of the filter residue from i-propanol/water gives 14.7 g (94%) of compound (104) (Table 1), m.p. 121–124° C.

EXAMPLE 5

Preparation of Compound (105) (Table 1)

The preparation is carried out analogously to the process described by S. Senda and K. Hirota, Chem. Pharm. Bull. 22 (12), 2921–28 (1974).

8.1 g (0.03 mol) of 6-dimethylmethylene(1,3-dimethyl-2,4-dioxo-1,2,3,4-tetrahydropyrrolo[2,3-d]pyrimidine) ammonium chloride [see Example 4] are added at room temperature to a solution of 210 ml of absolute ethanol, 2 g (0.065 mol) of sodium hydride (20% in paraffin oil) and 9.6 g (0.06 mol) of diethyl malonate. The reaction mixture is stirred at room temperature for 30 minutes and subsequently evaporated in a vacuum rotary evaporator. The residue is slurried with a mixture of 90 ml of water and 5 ml of glacial acetic acid and stirred for 15 minutes. The yellow precipitate is filtered off, washed with water and dried. Crystallization from dimethylformamide/ethanol gives 6.9 g (66%) of compound (105), m.p. 249–251° C.

EXAMPLE 6

Preparation of Compound (106) (Table 1)

A solution of 5.7 g (0.105 mol) of formic acid (85%) and 13.4 g (0.165 mol) of formaldehyde solution (37%) is added dropwise over the course of 60 minutes with stirring to a refluxing suspension of 18 g (0.10 mol) of 1,3-dimethyl-2H-pyrrolo[2,3-d]pyrimidine-2,4(3H)-dione [compound (122), Example 10] in 60 g of water. The reaction mixture is subsequently stirred at 100° C. for a further 6 hours, then cooled to 20° C. and diluted with 100 ml of water. The precipitate [lacuna] filtered off, washed with water and dried to constant weight. Crystallization of the residue from dimethylformamide gives 18.0 g (97%) of compound (106) (Table 1), pink crystals, m.p. >320° C.

Replacement of 1,3-dimethyl-2H-pyrrolo[2,3-d] pyrimidine-2,4(3H)-dione [compound (122)] by 2H-pyrrolo[2,3-d]pyrimidine-2,4(3H)-dione [compound (123), Example 10] in Example 6 gives compound (107) (Table 1).

Replacement of the formaldehyde solution by acetaldehyde, propionaldehyde or benzaldehyde in Example 6 gives compounds (108), (109) and (110) (Table 1).

EXAMPLE 7

Preparation of Compound (111) (Table 1)

The preparation is carried out analogously to the process described by S. Senda and K. Hirota, Chem. Pharm. Bull. 22 (7), 1459–1467 (1974).

13.5 g (0.06 mol) of a Schiff base made from 4-hydrazino-1,3-dimethyluracil and ethyl methyl ketone are mixed, with stirring, with 60 ml of ethylene glycol, and the mixture is kept at 190° C. for 1 hour. The reaction mixture is cooled, and 50 ml of i-propanol are added. The precipitate is filtered off, washed with i-propanol/petroleum ether and dried. Crystallization of the filter residue from ethanol/water gives 9.8 g (79%) of compound (111) (Table 1), white crystals, m.p. 318–320° C.

EXAMPLE 8

Preparation of Compound (112) (Table 1)

The preparation can be carried out analogously to the process described by H. Ogura, M. Sakaguchi and K. Takeda, Chem. Pharm. Bull. 20 (2), 404–408 (1972).

A mixture of 31 g (0.20 mol) of 4-amino-1,3-dimethyluracil, 40 g (0.20 mol) of phenacyl bromide and 250 ml of dimethylformamide is stirred at 135° C. for 2 hours. The reaction mixture is subsequently evaporated in a vacuum rotary evaporator. The residue is stirred with 200 ml of water, and the solid is filtered off, washed twice with 50 ml of water and dried to constant weight. Crystallization from glacial acetic acid/alcohol gives 46.2 g (91%) of compound (112) (Table 1), pale brown crystals, m.p. 289–296° C.

EXAMPLE 9

Preparation of Compounds (112) and (113) (Table 1)

The preparation can be carried out analogously to the process described by F. Yoneda, M. Higuchi, K. Senga, M. Kanohori and S. Nishigaki, Chem. Pharm. Bull. 21 (3), 473–477 (1973).

A mixture of 15.5 g (0.10 mol) of 4-amino-1,3-dimethyluracil, 19.9 g (0.10 mol) of phenacyl bromide and 150 ml of glacial acetic acid is stirred at 90° C. for 5 hours. The reaction mixture is subsequently evaporated in a vacuum rotary evaporator. The residue is slurried with 300 ml of water, and the insoluble material is filtered off, washed with water and dried. Crystallization of the residue from ethanol gives 16.7 g (65%) of compound (112) (Table 1), white crystals. The mother liquor is subsequently adjusted to pH 10 using ammonia solution (25%), and the mixture is stirred for 10 minutes. The resultant precipitate is filtered off, washed with water and dried. Crystallization of the filter residue from ethanol/water gives 3.5 g (14%) of compound (113), white crystals, m.p. 126–127° C.

Replacement of 4-amino-1,3-dimethyluracil by 4-aminouracil, 4-amino-3-n-propyluracil, 4-amino-1,3-di-n-propyluracil, 4-amino-1,3-di-n-butyl-2-thiouracil or 4-amino-1,3-diethyl-2-thiouracil in Example 9 gives compounds (114), (115), (116), (117) and (118) (Table 1).

EXAMPLE 10

Preparation of Compound (122) (Table 1)

A solution of 52.4 g (0.30 mol) of chloroacetaldehyde (45% aqueous solution) and 15.4 g (0.20 mol) of ammonium acetate in 50 ml of water is added dropwise over the course of 10 minutes at a temperature of 60–65° C. to a stirred mixture of 31 g (0.10 mol) of 4-amino-1,3-dimethyluracil, 15.4 g (0.20 mol) of ammonium acetate and 150 ml of water. A precipitate forms. The reaction mixture is stirred for a further 15 minutes, the stirrer is switched off, and the mixture is left to stand at room temperature for 12 hours. The precipitate is filtered off, washed with water and dried to constant weight, giving 23.6 g (66%) of compound (122) (Table 1) as a white powder, m.p. 288–292° C.

Replacement of 4-amino-1,3-dimethyluracil by 4-aminouracil, 4-amino-3-n-propyluracil or 4-amino-1,3-diethyluracil in Example 10 gives compounds (123), (124) and (125) (Table 1).

Replacement of chloroacetaldehyde by α-chloropropionaldehyde in Example 10 gives compound (126) (Table 1).

EXAMPLE 11

Preparation of a Mixture of Compounds (103) and (127)

A mixture of 31 g (0.20 mol) of 4-amino-1,3-dimethyluracil, 25.5 g (0.22 mol) of acetoxyacetone, 12.2 g (0.20 mol) of ethanolamine and 12 g (0.20 mol) of glacial acetic acid in 200 ml of water is refluxed for 9 hours. The reaction mixture is subsequently cooled to 10° C., and the precipitate is filtered off and dried to constant weight, giving 18.9 g of an approximately 1:1 mixture of compounds (103) and (127), white crystals, m.p. 246° C. The composition is determined by $^1$H-NMR.

EXAMPLE 12

Preparation of Compound (103) (Table 1)

A mixture of 31.0 g (0.10 mol) of 4-amino-1,3-dimethyluracil, 25.5 g (0.22 mol) of acetoxyacetone and 15.4 g (0.20 mol) of ammonium acetate in 200 ml of water is refluxed for 12 hours. The reaction mixture is subsequently cooled to 10° C., the precipitate is filtered off with suction, washed with 2×50 ml of water and dried at 60° C. in vacuo to constant weight, giving 28.6 g (74%) of compound (103), pale-beige crystals, m.p. 313–314° C. If the mother liquor is re-used as reaction medium with the same reaction procedure, the yield is increased to above 80% of theory.

Replacement of 4-amino-1,3-dimethyluracil by 4-amino-1,3-diethyluracil, 4-amino-3-n-propyluracil, 4-amino-1,3-di-n-butyluracil or 4-amino-1,3-di-n-propyluracil in Example 12 gives compounds (129), (130), (131) and (133) (Table 1).

Replacement of acetoxyacetone by 1-acetoxy-2-butanone [Beilstein EIII, Volume 2, page 360] in Example 12 gives compound (128) (Table 1).

Replacement of 4-amino-1,3-dimethyluracil and acetoxyacetone by 4-amino-1,3-diethyluracil and 1-acetoxy-2-butanone [Beilstein EIII, Volume 2, page 360] in Example 12 gives compound (132) (Table 1).

In the case of more highly alkylated aminouracils, a water-miscible solvent, for example n-propanol, dioxane or dimethylformamide, can be added to the reaction mixture.

EXAMPLE 13

Preparation of Compounds (134) and (135)

A mixture of 9.7 g (0.05 mol) of 1,3-dimethyl-2H-pyrrolo[2,3-d]pyrimidine-2,4(3H)-dione [compound (122), Example 10] and 13.2 g (0.05 mol) of 4-(dimethylaminomethylene)-2,6-di-tert-butylphenol in 60 ml of acetic acid is stirred at 120° C. for 4 hours. The reaction mixture is subsequently stirred for a further 30 minutes, and the crystals which precipitate are filtered. Crystallization of the residue from methanol gives 5.5 g (23%) of compound (134) (Table 1), white crystals, m.p. 233° C. The mother liquor is mixed with 200 ml of water, the mixture is stirred for 1.5 hours, and the precipitate is filtered off and dried. Crystallization of the residue from toluene gives 8.5 g (43%) of compound (135) (Table 1), white crystals, m.p. 250–260° C.

EXAMPLE 14

Preparation of Compound (134) (Table 1)

A mixture of 9.0 g (0.05 mol) of 1,3-dimethyl-2H-pyrrolo[2,3-d]pyrimidine-2,4(3H)-dione [compound (122), Example 10], 22.6 g (0.086 mol) of 4-(dimethylaminomethylene)-2,6-di-tert-butylphenol and 1 ml of sodium ethoxide solution (30%) in 100 ml of absolute ethanol is refluxed with stirring for 8 hours. The reaction mixture is subsequently cooled to 10° C., and the precipitated product is filtered off, washed with ethanol/petroleum ether and dried, giving 21.6 g (88% of compound (134) (Table 1), white crystals, m.p. 235–238° C.

EXAMPLE 15

Preparation of Compound (136) (Table 1)

17.9 g (0.10 mol) of 1,3-dimethyl-2H-pyrrolo[2,3-d]pyrimidine-2,4(3H)-dione [compound (122), Example 10] are added in portions at 40° C. with stirring to a freshly prepared magnesium methoxide solution prepared from 1.34 g (0.055 mol) of magnesium turnings and 150 ml of absolute methanol. The reaction mixture is subsequently refluxed for 2 hours and then cooled to 20° C. The precipitated product is filtered off, washed with methanol and petroleum ether and dried, giving 20 g (95%) of compound (136) (Table 1), pale-grey powder, m.p. >340° C. Mg determination: calculated: 6.4% of Mg; found: 7.0% of Mg.

Replacement of 1.4 g of magnesium by 2.2 g (0.055 mol) of calcium in Example 15 gives compound (138) (Table 1). Yield: 20.2 g (95%), pale powder, m.p.>340° C. Ca determination: calculated: 10.1%; found: 9.5%

EXAMPLE 16

Preparation of Compound (137) (Table 1)

A mixture of 5.4 g (0.03 mol) of 1,3-dimethyl-2H-pyrrolo[2,3-d]pyrimidine-2,4(3H)-dione [compound (122), Example 10] in 100 ml of absolute methanol is mixed with 5.4 g (0.03 mol) of a 30% sodium methoxide solution. The clear solution is subsequently evaporated in a vacuum rotary evaporator, giving 6.0 g (95%) of compound (137) (Table 1), grey powder, m.p. >340° C.

EXAMPLE 17

Preparation of Compound (139) (Table 1)

50 ml of acetic anhydride are added dropwise over the course of 75 minutes at about 10° C. with stirring to 57.5 g (0.25 mol) of hydroiodic acid (57% in water). 9.0 g (0.05 mol) of 1,3-dimethyl-2H-pyrrolo[2,3-d]pyrimidine-2,4(3H)-dione [compound (122), Example 10] and 5.7 g (0.04 mol) of di-n-butyl ketone are subsequently added. The reaction mixture is then stirred at 20° C. for 15 minutes and at about 40° C. for 120 minutes. After cooling, the reaction mixture is stirred into 500 ml of water, the aqueous phase is decanted off, and the residue is stirred for 1 hour in 500 ml of diethyl ether. The precipitate is filtered off and dried. Crystallization from n-propanol and purification using activated charcoal gives 10.0 g (83%) of compound (139) (Table 1), brown powder, m.p. 232–234° C.

Replacement of di-n-butyl ketone by acetone, methyl nonyl ketone or acetophenone in Example 17 gives compounds (140), (141) and (142) (Table 1).

EXAMPLE 18

Preparation of Compound (119) (Table 1)

a) 69.0 g (0.61 mol) of ethyl cyanoacetate are added under a nitrogen atmosphere to a solution of 86.08 g (0.50 mol) of O-methylisourea hydrogensulfate in 300 ml of absolute methanol. 216 g (1.20 mol) of a 30% solution of sodium methoxide in methanol is subsequently added dropwise. The reaction mixture warms to 57.5° C. The reaction mixture is subsequently refluxed for 5 hours, then cooled and left to stand overnight. The precipitated salts (NaHSO$_4$) are filtered off and the filtrate is evaporated in a vacuum rotary evaporator. The residue is taken up in about 300 ml of water with warming. As soon as a clear solution is present, the mixture is acidified (pH about 6) using about 35 ml of glacial acetic acid and then cooled in an ice/water bath, and the precipitated product is filtered off and washed with water. Drying of the residue in a vacuum drying cabinet gives 69.2 g (70.6%) of compound (119a), m.p. 232–235° C.

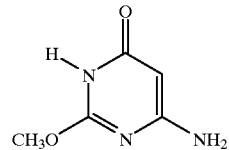

(119a)

b) A mixture of 7.1 g (0.05 mol) of compound (119a) [preparation, see Example 18a] and 10.0 g (0.05 mol) of phenacyl bromide in 70 ml of dimethylformamide is stirred at about 130° C. for 3 hours. The reaction mixture is subsequently cooled to room temperature. The precipitate is filtered off and dried, giving 3.7 g (30%) of compound (119) (Table 1), m.p. >350° C.

EXAMPLE 19

Preparation of Compound (120) (Table 1)

A solution of 15.5 g (0.10 mol) of 4-amino-1,3-dimethyluracil and 20.2 g (0.15 mol) of 1-chloro-3,3- dimethyl-2-butanone (Aldrich) in 75 ml of dimethylacetamide is stirred at 160° C. for 2.5 hours. After cooling, the mixture is clarified by filtration, and the filtrate is evaporated in a vacuum rotary evaporator. The residue is dissolved in methylene chloride and washed twice with water. The organic phase is dried over sodium sulfate and evaporated in a vacuum rotary evaporator. Chromatography of the residue on silica gel gives 3.5 g (15%) of compound (120) (Table 1), yellow crystals, m.p. 226–232° C.

EXAMPLE 20

Preparation of Compound (121) (Table 1)

A mixture of 15.5 g (0.10 mol) of 4-amino-1,3-dimethyluracil and 23.4 [lacuna] (0.11 mol) of α-bromopropiophenone (Aldrich) in 100 ml of dimethylformamide is stirred at about 130° C. for 3 hours. The reaction mixture is subsequently cooled and evaporated in a vacuum rotary evaporator. 100 ml of ethanol are added to the residue. The precipitate is filtered and washed with ethanol and methyl tert-butyl ether. Crystallization from n-butanol gives 11.4 g (42%) of compound (121) (Table 1), yellow crystals, m.p. 270–272° C.

EXAMPLE 21

Preparation of Compound (103) (Table 1)

101 g (1.32 mol) of hydroxyacetone are added dropwise over the course of 90 minutes under reflux and with stirring to a mixture of 186 g (1.20 mol) of 4-amino-1,3-dimethyluracil and 23.1 g (0.30 mol) of ammonium acetate in 72 g (1.20 mol) of glacial acetic acid and 185 g of water. The mixture is subsequently refluxed for 3 hours. The reaction mixture is cooled, the precipitate is filtered off, and the residue is washed with 3×80 ml of water and subsequently dried, giving 188 g (81%) of compound (103), beige crystals, m.p. 313–314° C.

Replacement of hydroxyacetone by hydroxy-3,3-dimethylbutanone [J. Org. Chem. 1993 (58), 7557], 3-hydroxy-2-butanone (Aldrich), ω-hydroxyacetophenone [J. Org. Chem. 1993 (58), 7557] and 2,5-dimethyl-2,5-dimethoxy-1,4dioxane [Houben-Weyl VII/2a, page 828] in Example 21, gives compounds (128) (yield 84%); (120) (yield 25%); (111) (yield 32%); (112) (yield 94%); and (103) (yield 84%).

EXAMPLE 22

Preparation of Compound (131) (Table 1)

A solution of 19.2 g (0.22 mol) of hydroxyacetone (85%) in 15 g of n-propanol is added dropwise in the course of 100 minutes under reflux and with stirring to a mixture of 48 g (0.20 mol) of 4-amino-1,3-di-n-butyluracil and 15.4 g (0.20 mol) of ammonium acetate in 36 g of glacial acetic acid and 130 g of water. The mixture is subsequently refluxed for 6 hours. The reaction mixture is cooled, and 300 ml of methylene chloride are added. The organic phase is separated off, washed with water, sodium hydrogencarbonate solution and again with water, dried over sodium sulfate and evaporated in a vacuum rotary evaporator. The residue gives 46.0 g of a mixture comprising 84 mol % of compound (131) and 16 mol % of starting material (4-amino-1,3-di-n-butyluracil) as pale-brown crystals. The composition is determined by $^1$H-NMR spectrum.

EXAMPLE 23

Preparation of Compound (143) (Table 1)

A solution of 10.2 g (1.10 mol) of hydroxy-2-butanone in 10 ml of water is added dropwise over the course of 50 minutes under reflux and with stirring to a mixture of 22.9 g (0.10 mol) of 4-amino-1,3-di-n-propyluracil and 7.7 g (0.10 mol) of ammonium acetate in 25 g of glacial acetic acid and 50 g of water. The mixture is subsequently refluxed for 3 hours. The reaction mixture is cooled, and 500 ml of water are added. The organic phase is extracted with 100 ml of methylene chloride. The organic phase is separated off, washed with water, sodium hydrogencarbonate solution and again with water, dried over sodium sulfate and evaporated in a vacuum rotary evaporator. Crystallization of the residue from ethyl acetate gives 8.8 g (34%) of compound (143) (Table 1), white crystals, m.p. 141–142° C.

EXAMPLE 24

Preparation of Compound (144) (Table 1)

A mixture of 39.9 g (0.20 mol) of 4-amino-1,3-diethylthiouracil, 22.9 g (0.30 mol) of hydroxyacetone, 23.1 [lacuna] (0.30 mol) of ammonium acetate, 30 g of acetic acid and 50 g of water is refluxed with stirring for 18 hours. The reaction mixture is subsequently cooled, and the precipitate is filtered off. The tacky precipitate is boiled with 50 ml of n-propanol, and then cooled, the insoluble material is filtered, and the residue is washed with petroleum ether. Drying gives 3.3 g (6.9%) of compound (144) (Table 1), beige crystals, m.p.301–303° C.

EXAMPLE 25

Preparation of Compound (146) (Table 1)

A mixture of 31.1 g (0.20 mol) of 4-amino-1,3-dimethyluracil, 39.6 g (0.22 mol) of a 40% aqueous methylglyoxal solution and 150 ml of water is stirred at room temperature for 3 hours. The precipitate is subsequently filtered, washed with water and n-propanol and dried to constant weight, giving 31.6 g (91.3%) of compound (146) (Table 1), white crystals, m.p. >330° C.

Replacement of methylglyoxal solution by glyoxal (Aldrich) or diacetyl (Aldrich) in Example 25 gives compounds (145) and (147) (Table 1).

Furthermore, replacement of methylglyoxal solution by 2,3-hexanedione, 3,4hexanedione (Aldrich) or phenylglyoxal and addition in each case of 50 ml of acetic acid in Example 25 gives compounds (148), (149) and (151). Compound (149) is worked up after the reaction by evaporation of the reaction mixture to residue.

EXAMPLE 26

Preparation of Compound (150) (Table 1)

A mixture of 31.0 g (0.20 mol) of 4-amino-1,3-dimethyluracil, 38.8 g (0.22 mol) of ethyl diethoxyacetate (Aldrich), 7.7 g (0.10 mol) of ammonium acetate, 150 ml of water and 50 g of acetic acid is refluxed for 7.5 hours. The reaction mixture is subsequently cooled, the precipitate is filtered, and the residue is washed with water and then slurried with 100 ml of acetone. The product is again filtered, and the residue is washed with acetone and dried to constant weight, giving 14.2 g (41%) of compound (150), beige crystals, m.p. 276–279° C.

EXAMPLE 27

Preparation of Compound (152) (Table 1)

a) 50.5 g (0.40 mol) of 6-methyluracil (Merck) are introduced in portions over the course of one hour with stirring at 0 to +5° C. into a solution of 200 ml of 100% nitric acid (fuming) and 50 g of phosphorus pentoxide. When the exothermic reaction is complete, the mixture is stirred at +5° C. for a further 5 hours. The reaction mixture is subsequently poured into 1 kg of ice-water. The resultant precipitate is filtered, washed with water and then dried to constant weight, giving 37 g (54%) of 5-nitro-6-methyluracil, pale-yellow powder, m.p. 281° C. with decomposition.

b) 171 g (1.00 mol) of 5-nitro-6-methyluracil (Example 27a) are introduced in portions with stirring at room temperature into 40 g (1.0 mol) of 2N sodium hydroxide solution, the initially clear solution becoming cloudy with slight evolution of heat. Under strict temperature and pH control (T=40° C.; pH=8–9), 400 g (3.2 mol) of dimethyl sulfate and 4N sodium hydroxide solution are simultaneously added dropwise over the course of 3 hours with stirring. Stirring of the reaction mixture is continued, and the resultant precipitate is left to stand overnight and then filtered. The residue is washed with water and then dried to constant weight, giving 97 g (49%) of 5-nitro-1,3,6-trimethyluracil, pale-yellow powder, m.p. 152° C.

c) 39.8 g (0.20 mol) of 5-nitro-1,3,6-trimethyluracil (Example 27b) are refluxed for one hour with stirring in 150 ml of absolute ethanol containing 17.4 g of sodium ethoxide. The mixture is then cooled to room temperature, and filtered, and the residue is washed with warm ethanol and then dried to constant weight, giving 44.3 g (99%) of the sodium salt of 5-nitro-1,3,6-trimethyluracil as a yellow powder.

d) A mixture of 22.1 g (0.10 mol) of the sodium salt of 5-nitro-1,3,6-trimethyluracil (Example 27c), 15.2 g (0.12 mol) of benzyl chloride, 15.2 g (0.11 mol) of potassium carbonate and 6.1 g (0.036 mol) of potassium iodide in 150 ml of dimethylformamide is kept at 120° C. for 4 hours with stirring. The volatile components are then removed in a vacuum rotary evaporator, 400 g of ice-water are added to the residue, and the mixture is acidified using 50 g of acetic acid with stirring. The resultant precipitate is filtered, and the residue is washed with water until neutral and dried to constant weight. This residue is dissolved in 250 ml of dimethylformamide and refluxed for 2 hours. The reaction mixture is subsequently evaporated in a vacuum rotary evaporator. The residue is taken up in 150 ml of hot ethanol. The precipitate is filtered, and the filter residue is washed with ethanol and dried to constant weight, giving 8.94 g (35%) of compound (152) (Table 1), beige powder, m.p. 314° C.

Replacement of benzyl chloride by 4-tert-butylbenzyl chloride in Example 27d gives compound (153) (Table 1), yield 20%, m.p. 307° C.

TABLE 1

| No. | Compound | m.p.(° C.) |
|---|---|---|
| 101 | (structure) ·$H_2O$ | 228–232 |
| 102 | (structure) | 310 |
| 103 | (structure) | 313–314 |
| 104 | (structure) | 121–124 |

TABLE 1-continued

| No. | Compound | m.p.(° C.) |
|---|---|---|
| 105 | (structure) | 249–251 |
| 106 | (structure) | >320 |
| 107 | (structure) | >350 |
| 108 | (structure) | 325–328 |
| 109 | (structure) | >320 |
| 110 | (structure) | 281–287 |
| 111 | (structure) | 318–320 |

TABLE 1-continued

| No. | Compound | m.p.(° C.) |
|---|---|---|
| 112 | | 289–296 |
| 113 | | 126–127 |
| 114 | | >350 |
| 115 | | 293–302 |
| 116 | | 92–97 |
| 117 | | 173–177 |

TABLE 1-continued

| No. | Compound | m.p.(° C.) |
|---|---|---|
| 118 | | 267–270 |
| 119 | | >350 |
| 120 | | 226–232 |
| 121 | | 270–272 |
| 122 | | 288–292 |
| 123 | | >350 |
| 124 | | 263 (decomp.) |

TABLE 1-continued

| No. | Compound | m.p.(° C.) |
|---|---|---|
| 125 | [structure: 1,3-diethyl pyrrolo-pyrimidinedione] | 185–188 (decomp.) |
| 126 | [structure: 1,3-dimethyl-5-methyl pyrrolo-pyrimidinedione] | 320–323 |
| 127 | [structure: 1,3-dimethyl-6-methyl-7-(2-hydroxyethyl) pyrrolo-pyrimidinedione] | not isolated in pure form, only as a mixture with compound (103) (Example 11) |
| 128 | [structure: 1,3-dimethyl-6-ethyl pyrrolo-pyrimidinedione] | 295–297 |
| 129 | [structure: 1,3-diethyl-6-methyl pyrrolo-pyrimidinedione] | 226–227 |
| 130 | [structure: 1-propyl-6-methyl pyrrolo-pyrimidinedione] | 312–314 |
| 131 | [structure: 1,3-dibutyl-6-methyl pyrrolo-pyrimidinedione] | 196–197 |

TABLE 1-continued

| No. | Compound | m.p.(° C.) |
|---|---|---|
| 132 | (structure) | 250–252 |
| 133 | (structure) | 211–231 |
| 134 | (structure) | 235–238 |
| 135 | (structure) | 250–260 |
| 136 | (structure with Mg$^{2+}$) | >340 |
| 137 | (structure with Na$^+$) | >340 |

TABLE 1-continued
| No. | Compound | m.p.(° C.) |
|---|---|---|
| 138 | 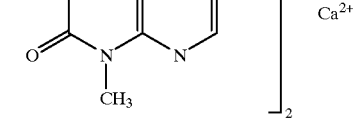 | >340 |
| 39 | 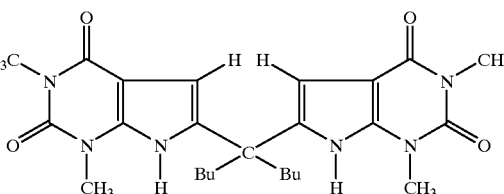<br>Bu = n-butyl (CH₃CH₂CH₂CH₂-) | 270–272<br>(CH₃OH/water) |
| 140 | 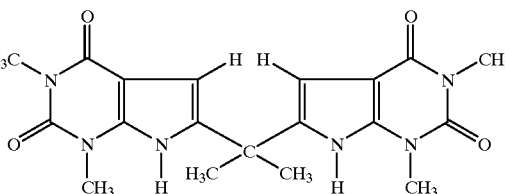 | 333–335 |
| 141 | 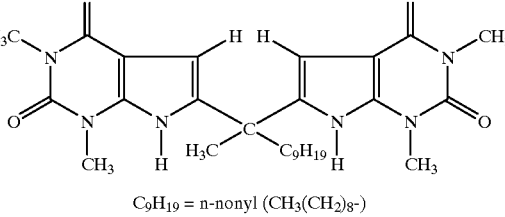<br>C₉H₁₉ = n-nonyl (CH₃(CH₂)₈-) | 268–270 |
| 142 | 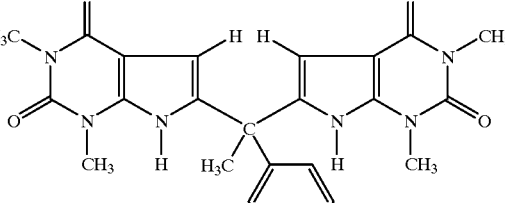 | 291–295 |
| 143 | 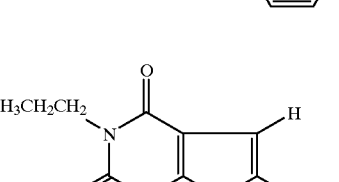 | 141–142 |

TABLE 1-continued

| No. | Compound | m.p.(° C.) |
| --- | --- | --- |
| 144 | (structure) | 301–303 |
| 145 | (structure) | 325–335 |
| 146 | (structure) | >330 |
| 147 | (structure) | 317–318 (decomposition) |
| 148 | (structure) | 284 (decomposition) |

TABLE 1-continued

| No. | Compound | m.p.(° C.) |
|---|---|---|
| 149 | [structure] | amorphous powder |
| 150 | [structure] | 276–279 (decomposition) |
| 151 | [structure] | >340 |
| 152 | [structure] | 314 (decomposition) |
| 153 | [structure] | 307 |

EXAMPLE 28

Heat Test at 190° C.

A dry mixture comprising 100.0 parts of polyvinyl chloride (S-PVC, K value 60), 5.0 parts of epoxidized soybean oil, 0.8 part of a 1:1 mixture of didecyl phenyl phosphite and decyl diphenyl phosphite; 0.2 part of montanic acid ester and 1.0 part of a novel stabilizer from Table 1 is plasticated for 5 minutes at 170° C. on mixing rolls. Test specimens with a thickness of 0.5 mm are then cut out of the centre of the film and heated at 190° C. for the time shown in Table 2 in a Mathis Thermo-Takter. The yellowness index (YI) of these specimens is determined in accordance with ASTM D 1925-70. Low YI values denote little discoloration, while high YI values denote strong discolouration of the samples. The less the discoloration, the more effective the stabilizer. The results are shown in Table 2.

TABLE 2

Heat test, YI values after heating at 190° C.

| Stabilizer | Duration (minutes) | | | | | | |
|---|---|---|---|---|---|---|---|
| | 0 | 5 | 10 | 15 | 20 | 25 | 30 |
| — | 53.4 | 66.5 | 81.7 | 114.6 | 125.8 | 143.4 | destroyed |
| 103 | 10.9 | 11.9 | 14.2 | 17.4 | 23.6 | 35.9 | 42.0 |
| 112 | 15.3 | 23.2 | 29.2 | 34.1 | 48.2 | 56.1 | 62.9 |
| 128 | 11.3 | 11.4 | 14.9 | 22.2 | 30.8 | 41.2 | 51.2 |
| 129 | 5.9 | 6.0 | 7.5 | 11.5 | 18.7 | 30.3 | 43.8 |
| 130 | 22.0 | 28.3 | 33.1 | 36.9 | 45.7 | 53.8 | 55.2 |
| 131 | 7.3 | 6.9 | 8.9 | 14.5 | 23.4 | 34.1 | 46.6 |
| 132 | 9.1 | 11.5 | 14.4 | 22.5 | 34.7 | 50.1 | 64.4 |

A further determination of the stability is effected by the dehydrochlorination test, which is carried out in accordance with DIN 53381, Part 3. In this test, the time taken for the dehydrochlorination curve to rise (induction time, IT) and time taken for the conductivity to exceed 200 $\mu S$ (stabilization time, ST) are determined at 190° C. The results are shown in Table 3. The higher the values, the more effective the stabilizer.

TABLE 3

Dehydrochlorination test at 190° C.

| Stabilizer | Induction time (IT) in minutes | Stabilization time (ST) in minutes |
|---|---|---|
| — | 46.0 | 50.5 |
| 103 | 83.0 | 89.5 |
| 112 | 69.0 | 76.0 |
| 128 | 75.0 | 82.5 |
| 129 | 79.0 | 86.0 |
| 130 | 63.5 | 68.0 |
| 131 | 74.0 | 81.5 |
| 132 | 71.5 | 79.5 |

A further determination of the stability is effected by pressing the films at 180° C. and 200 bar for 3 minutes to give sheets with a thickness of 3 mm (pressed sheet test), and the yellowness index of the sheets is determined in accordance with ASTM D 1925-70. The results are shown in Table 4. Low YI values denote little discoloration, high YI values strong discoloration of the samples. The less discoloration, the more effective the stabilizer.

TABLE 4

Pressed sheet test

| Stabilizer | YI values |
|---|---|
| — | 134.0 |
| 103 | 44.3 |
| 112 | 59.6 |
| 128 | 46.6 |
| 129 | 30.2 |
| 131 | 35.3 |
| 132 | 46.0 |

What is claimed is:

1. A process for the preparation of a compound having the formula

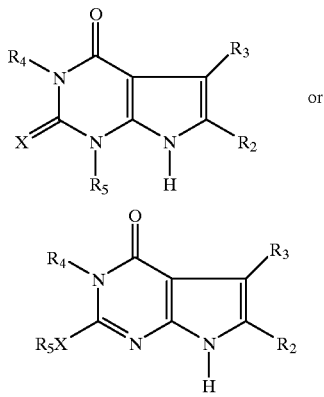

wherein $R_2$ and $R_3$ are the same or different and are hydrogen, $C_1$–$C_{12}$ alkyl, $C_2$–$C_{12}$ alkyl which is interrupted by oxygen, sulfur or carbonyl, hydroxyl-substituted $C_1$–$C_{12}$ alkyl, $C_3$–$C_6$ alkenyl, $C_5$–$C_8$ cycloalkyl, $C_5$–$C_8$ cycloalkyl substituted by one to three $R_6$ radicals, phenyl, phenyl substituted by one to three $R_6$ radicals, $C_7$–$C_9$ phenylalkyl or $C_7$–$C_9$ phenylalkyl whose phenyl ring is substituted by one to three $R_6$ radicals,

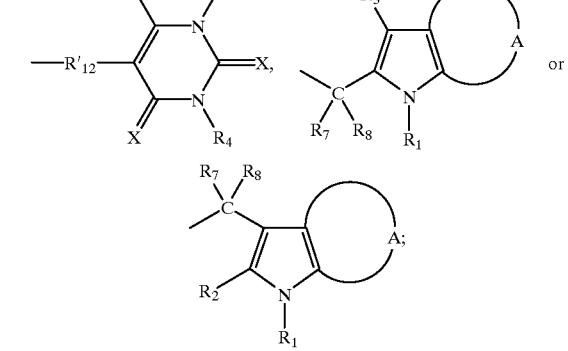

or one of $R_2$ and $R_3$ is hydroxyl, formyl, $C_1$–$C_{12}$ alkoxy, phenoxy, phenoxy substituted with one to three $R_6$ radicals, $C_1$–$C_{12}$ alkanoyloxy, benzoyloxy, benzoyloxy substituted with one to three $R_6$ radicals,

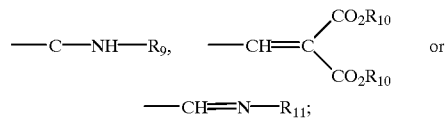

A is

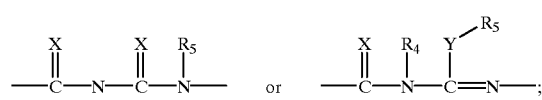

X is oxygen or sulfur; Y is oxygen, sulfur or

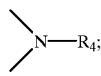

$R_4$ and $R_5$ are the same or different and are hydrogen, $C_1$–$C_{12}$ alkyl, $C_2$–$C_{12}$ alkyl interrupted by oxygen, sulfur or carbonyl, hydroxyl-substituted $C_1$–$C_{12}$ alkyl, $C_3$–$C_6$alkenyl, $C_5$–$C_8$ cycloalkyl, $C_5$–$C_8$ cycloalkyl substituted with one to three $R_6$ radicals, phenyl, phenyl substituted with one to three $R_6$ radicals, $C_7$–$C_9$ phenylalkyl or $C_7$–$C_9$ phenylalkyl substituted on the phenyl ring with one to three $C_6$ radicals; $R_6$ is $C_1$–$C_4$ alkyl, $C_1$–$C_4$ alkoxy, $C_5$–$C_8$ cycloalkyl, hydroxyl or chlorine; $R_7$ and $R_8$ are the same or different and are hydrogen, $CF_3$, $C_1$–$C_{12}$ alkyl, phenyl or $C_7$–$C_9$ phenylalkyl or are, together with a carbon atom to which they are bonded, a $C_5$–$C_{12}$ cycloalkylidene ring or a $C_5$–$C_{12}$ cycloalkylidene ring substituted with $C_1$–$C_4$ alkyl; $R_9$ is phenyl or phenyl substituted with one to three $R_6$ radicals; $R_{10}$ is hydrogen, $C_1$–$C_{12}$ alkyl, $C_2$–$C_{12}$ alkyl interrupted by oxygen or sulfur, $C_1$–$C_{12}$ alkyl substituted with hydroxyl, $C_3$–$C_6$ alkenyl, $C_5$–$C_8$ cycloalkyl, $C_5$–$C_8$ cycloalkyl substituted with one to three $R_6$ radicals, phenyl, phenyl substituted with one to three $R_6$ radicals, $C_1$–$C_9$ phenylalkyl or $C_7$–$C_9$ phenylalkyl substituted on the phenyl ring by one to three $R_6$ radicals; $R_{11}$ is $C_1$–$C_{12}$ alkyl, $C_2$–$C_{12}$ alkyl interrupted by oxygen or sulfur, $C_1$–$C_{12}$ alkyl substituted with hydroxyl, $C_3$–$C_6$ alkenyl, $C_5$–$C_8$ cycloalkyl, $C_5$–$C_8$ cycloalkyl substituted with one to three $R_6$ radicals, phenyl, phenyl substituted with one to three $R_6$ radicals, $C_7$–$C_9$ phenylalkyl or $C_7$–$C_9$ phenylalkyl substituted on the phenyl ring by one to three $R_6$ radicals; $R'_{12}$ is a direct bond or

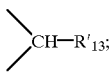

and $R'_{13}$ is hydrogen or $C_1$–$C_8$, alkyl, which comprises reacting a compound selected from the group consisting of

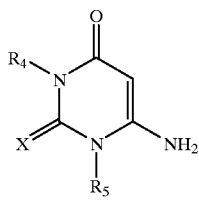 and 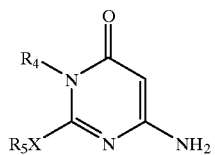

in which $R_4$, $R_5$ and X have the meanings given above, with a compound selected from the group consisting of

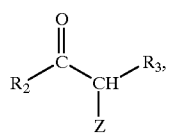 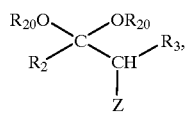

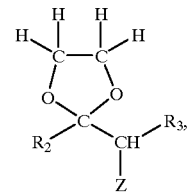 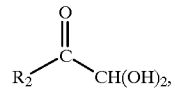

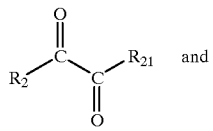 and 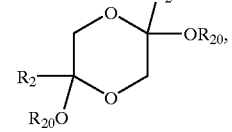

where $R_2$ and $R_3$ have the meanings defined above; $R_{20}$ is $C_1$–$C_4$ alkyl; $R_{21}$ is $C_1$–$C_{14}$ alkyl; and Z is a leaving group, in the presence of an ammonium salt.

2. A process according to claim 1, in which the leaving group Z is halogen, hydroxyl or

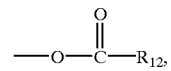

$R_{12}$ is hydrogen, $C_1$–$C_4$alkyl or unsubstituted or $R_{13}$-substituted phenyl; and $R_{13}$ is halogen, nitro, $CF_3$, $C_1$–$C_4$alkyl or $C_1$–$C_4$alkoxy.

3. A process according to claim 1, in which the ammonium salt is a compound of the formula

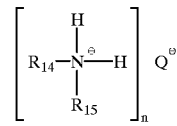

in which
n is 1 or 2,
$R_{14}$ and $R_{15}$, independently of one another, are hydrogen, $C_1$–$C_{12}$alkyl, $C_2$–$C_{12}$alkyl which is interrupted by oxygen or sulfur; hydroxyl-substituted $C_1$–$C_{12}$alkyl; $C_3$–$C_6$alkenyl, $C_5$–$C_8$cycloalkyl which is unsubstituted or substituted by one to three $R_{16}$ radicals; phenyl which is unsubstituted or substituted by one to three $R_{16}$ radicals; $C_7$–$C_9$phenylalkyl which is unsubstituted or substituted on the phenyl ring by one to three $R_{16}$ radicals; or $R_{14}$ and $R_{15}$, together with the nitrogen atom to which they are bonded, form a $C_4$–$C_7$cycloalkylene ring, which may additionally be interrupted by oxygen or sulfur,
$R_{16}$ is $C_1$–$C_4$alkyl, $C_1$–$C_4$alkoxy, $C_5$–$C_8$cycloalkyl, hydroxyl or chlorine, and if n=1,
$Q^\ominus$ is

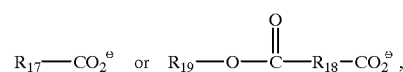

and
if n=2,
$Q^\ominus$ is carbonate or $^\ominus O_2C$—$R_{18}$—$CO_2^\ominus$,
$R_{17}$ is hydrogen, hydroxyl, $C_1$–$C_{18}$alkyl, phenyl or benzyl, $R_{18}$ is a direct bond or $C_1$–$C_6$alkylene, and
$R_{19}$ is hydrogen or $C_1$–$C_{18}$alkyl.

4. A process according to claim 1 in which, when the reaction is complete, a mixture comprising a precipitate of said compound having the formula

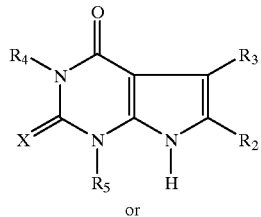

or

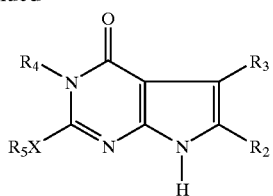

and a mother liquor is formed, and said mother liquor is separated from said precipitate and used as a reaction medium in a further reaction according to claim 1.

* * * * *